US008257703B2

(12) United States Patent
Irie et al.

(10) Patent No.: US 8,257,703 B2
(45) Date of Patent: Sep. 4, 2012

(54) ANTI-GANGLIOSIDE ANTIBODIES AND COMPOSITIONS

(75) Inventors: Reiko Irie, Pacific Palisades, CA (US); Hiroyuki Tsunoda, Shizuoka (JP); Tomoyuki Igawa, Shizuoka (JP); Yasuo Sekimori, Shizuoka (JP); Masayuki Tsuchiya, Shizuoka (JP)

(73) Assignee: Chugai Seiyaku Kabushiki Kaisha, Tokyo (JP)

(\*) Notice: Subject to any disclaimer, the term of this patent is extended or adjusted under 35 U.S.C. 154(b) by 11 days.

(21) Appl. No.: 12/727,162

(22) Filed: Mar. 18, 2010

(65) Prior Publication Data

US 2010/0172899 A1 Jul. 8, 2010

Related U.S. Application Data

(62) Division of application No. 10/564,665, filed as application No. PCT/JP2004/010444 on Jul. 15, 2004, now Pat. No. 7,709,615.

(60) Provisional application No. 60/487,333, filed on Jul. 15, 2003.

(51) Int. Cl.
*A61K 39/395* (2006.01)

(52) U.S. Cl. ..................................... 424/130.1

(58) Field of Classification Search .................. None
See application file for complete search history.

(56) References Cited

U.S. PATENT DOCUMENTS

| 5,157,113 | A | | 10/1992 | Dove et al. |
| 5,190,752 | A | | 3/1993 | Möller et al. |
| 5,547,853 | A | | 8/1996 | Wallner et al. |
| 5,792,838 | A | | 8/1998 | Smith et al. |
| 5,830,470 | A | * | 11/1998 | Nakamura et al. ......... 424/133.1 |
| 5,908,826 | A | | 6/1999 | Fukuda et al. |
| 6,136,312 | A | | 10/2000 | Rentsch |
| 6,238,891 | B1 | | 5/2001 | Maiorella et al. |
| 2002/0119530 | A1 | | 8/2002 | Maiorella et al. |
| 2004/0081972 | A1 | | 4/2004 | Satoh et al. |
| 2004/0170623 | A1 | | 9/2004 | Arvinte et al. |
| 2005/0118167 | A1 | | 6/2005 | Okada et al. |
| 2006/0127395 | A1 | | 6/2006 | Arvinte et al. |
| 2007/0154469 | A1 | | 7/2007 | Irie et al. |
| 2007/0212346 | A1 | | 9/2007 | Igawa et al. |
| 2007/0249812 | A1 | | 10/2007 | Hayasaka et al. |
| 2009/0285802 | A1 | | 11/2009 | Igawa et al. |

FOREIGN PATENT DOCUMENTS

| CA | 2057842 A1 | 6/1992 |
| EP | 0 352 500 | 1/1990 |
| EP | 0 492 409 | 7/1992 |
| EP | 0 531 539 | 3/1993 |
| EP | 1 174 148 | 1/2002 |
| EP | 1 176 195 | 1/2002 |
| EP | 0841067 B1 | 5/2002 |
| EP | 1226752 A1 | 7/2002 |
| JP | 2-000493 | 1/1990 |
| JP | 2-078635 | 3/1990 |
| JP | 2501116 | 4/1990 |
| JP | 04-360696 | 12/1992 |
| JP | 5-065233 | 3/1993 |
| JP | 5192181 A | 8/1993 |
| JP | 6178689 A | 6/1994 |
| JP | 6-189781 | 7/1994 |
| JP | 6-205694 | 7/1994 |
| JP | 7-502497 | 3/1995 |
| JP | 9-127112 | 5/1997 |
| JP | 9-127114 | 5/1997 |
| JP | 10324699 A | 12/1998 |
| JP | 2000154149 A | 6/2000 |
| JP | 2000516470 A | 12/2000 |
| JP | 2001-504092 | 3/2001 |
| JP | 2002037800 A | 2/2002 |
| JP | 2002504342 A | 2/2002 |
| JP | 2002509122 A | 3/2002 |
| JP | 2002527100 A | 8/2002 |
| JP | 2003128576 A | 5/2003 |
| WO | WO 89/01975 | 3/1989 |
| WO | WO 89/04867 | 6/1989 |
| WO | WO 91/18106 | 11/1991 |
| WO | WO 93/08837 | 5/1993 |
| WO | 9419457 A1 | 9/1994 |
| WO | WO9806749 A2 | 2/1998 |
| WO | WO 99/37329 | 7/1999 |
| WO | WO9936105 A2 | 7/1999 |
| WO | WO9942597 A1 | 8/1999 |
| WO | WO023472 A2 | 4/2000 |
| WO | WO 00/61739 | 10/2000 |
| WO | WO 00/66160 | 11/2000 |
| WO | WO 01/23431 | 4/2001 |
| WO | WO0133957 A1 | 5/2001 |
| WO | WO0177342 A1 | 10/2001 |
| WO | WO0210371 A1 | 2/2002 |
| WO | WO 02/96457 | 12/2002 |
| WO | WO 03/046162 | 6/2003 |
| WO | 20050005636 A1 | 1/2005 |
| WO | WO 2005/005636 | 1/2005 |
| WO | 20050035573 A1 | 4/2005 |
| WO | 20050035574 A1 | 4/2005 |
| WO | WO 2005/035573 | 4/2005 |
| WO | WO 2005/035574 | 4/2005 |

OTHER PUBLICATIONS

Matsuuchi et al., "Immunoglobulin J chain gene from the mouse," *Proc. Natl. Acad. Sci. U.S.A.*, 83(2):456-60 (1986).

(Continued)

*Primary Examiner* — Ilia Ouspenski
(74) *Attorney, Agent, or Firm* — Fish & Richardson P.C.

(57) ABSTRACT

IgM can be obtained in the form of a pentamer by placing the genes encoding the H, L, and J chains on the same vector to transform appropriate host cells. The gene encoding the J chain may be introduced by co-transfection. When no J chain is expressed, the IgM is produced as a hexamer. The transformants obtained according to the present invention achieve a high yield of IgM. The present invention also provides methods which enable separation and quantification of polymeric IgM.

20 Claims, 5 Drawing Sheets

OTHER PUBLICATIONS

Azuma et al., "Recombinant Human Hexamer-Dominant IgM Monoclonal Antibody to Ganglioside GM3 for Treatment of Melanoma," Clin. Cancer Res., 13(9):2745-2750 (2007).
Irie et al., "Human Monoclonal Antibody to Ganglioside GM2 for Melanoma Treatment," Lancet, 1(8641):786-787 (1989).
Nishinaka et al., "Development of a Human Monoclonal Antibody for Ganglioside GM2 with Potential for Cancer Treatment," Cancer Research, 56(24):5666-5671 (1996).
Nishinaka et al., "Human IgM antibodies to tumor-associated gangliosides share VHIII (V3-V23) and VKIV family subgroups," Immunogenetics, 48(1):73-75 (1998).
European Search Report for App. U.S. Appl. No. 10/150,954, dated May 12, 2010, 5 pages.
Shitara et al., "A new vector for the high level expression of chimeric antibodies in myeloma cells," J. Immunol. Methods., 167(1-2):271-8 (1994).
USPTO Notice of Allowance in U.S. App. No. 10/574,827, dated May 4, 2010, 7 pages.
Okada, "Preparation of IgM Antibody-Producing Cell Lines that React to Hiv-Infected Cell Lines," Japan Health Science Foundation, 108-110 (1998).
Arya et al., "Mapping of Amino Acid Residues in the Cµ3 Domain of Mouse IgM Important in Macromolecular Assembly and Complement-Dependent Cytolysis," J. Immunol., 152:1206-12 (1994).
Brewer et al., "Mechanism and Subcellular Localization of Secretory IgM Polymer Assembly," J. Biol. Chem., 269:17338-48 (1994).
Cattaneo et al., "Polymeric Immunoglobulin M is Secreted by Transfectants of Non-Lymphoid Cells in the Absence of Immunoglobulin J Chain," EMBO J., 6:2753-58 (1987).
Chen et al. "Strategies to Suppress Aggregation of Recombinant Keratinocyte Growth Factor During Liquid Formulation Development," J. Pharm. Sci., 83:1657-1661 (1994).
Dráber et al., "Stability of Monoclonal IgM Antibodies Freeze-Dried in the Presence of Trehalose," Journal of Immunological Methods, 181:37-43 (1995).
García-González et al., "Purification of Murine IgG3 and IgM Monoclonal Antibodies by Euglobulin Precipitation," Journal of Immunological Methods, 111:17-23 (1988).
Gombotz et al., "The Stabilization of a Human IgM Monoclonal Antibody with Poly(vinylpyrrolidone)," Pharm. Res. 11:624-632 (1994).
Green, "Antibody engineering via genetic engineering of the mouse: XenoMouse strains are a vehicle for the facile generation of therapeutic human monoclonal antibodies," J. Immunol. Methods, 231:11-23 (1999).
Haruta et al., "Class-Switching of the IgM Type Anit-Adenocarcinoma Human Antibody HB4C5 into an IgG1 Type Resulted in the Loss of the Antigen Binding Ability," Human Antibodies, 8:137-145 (1997).
Hoon et al., "Molecular cloning of a human monoclonal antibody reactive to ganglioside GM3 antigen on human cancers," Cancer Res., 53:5244-50 (1993).
Huang et al., "Production of Recombinant Murine-Human Chimeric IgM and IgG Anti-Js$^b$ for Use in the Clinical Laboratory," Transfusion, 43:758-764 (2003).
Hughey et al., "Production of IgM Hexamers by Normal and Autoimmune B Cells: Implications for the Physiologic Role of Hexameric IgM," J. Immunol., 161:4091-97 (1998).
Irie et al., "Phase I pilot clinical trial of human IgM monoclonal antibody to ganglioside GM3 in patients with metastatic melanoma," Cancer Immunol. Immunother., 53:110-117 (2004).
Jones et al., "Replacing the complementarity-determining regions in a human antibody with those from a mouse," Nature, 321:522-525 (1986).
Kallemuchikkal et al., "Evaluation of cryoglobulins," Arch. Pathol. Lab. Med., 123:119-125 (1999).
Kunert et al., "Characterization of Molecular Features, Antigen-Binding, and In Vitro Properties of IgG and IgM Variants of 4E10, an Anti-HIV Type 1 Neutralizing Monoclonal Antibody," AIDS Res. Hum. Retroviruses, 20:755-762 (2004).
Mayus et al., "Inhibition of In Vitro Anti-DNA B-Cell Responses by Cyclosporine," Cell. Immunol., 94:195-204 (1985).
Meng et al., "J Chain Deficiency in Human IgM Monoclonal Antibodies Produced by Epstein-Barr Virus-Transformed B Lymphocytes," Eur. J. Immunol., 20:2505-08 (1990).
Middaugh et al., "Effect of solutes on the cold-induced insolubility of monoclonal cryoimmunoglobulins," J. Biol. Chem., 252:8002-06 (1977).
Middaugh et al., "Molecular basis for the temperature-dependent insolubility of cryoglobulins. IV. Structural studies of the IgM monoclonal cryoglobulin McE," Immunochem., 15:171-187 (1978).
Molina et al., "The Effects of Divalent Cations in the Presence of Phosphate, Citrate and Chloride on the Aggregation of Soy Protein Isolate," Food Research International, 32:135-143 (1999).
Monica et al., "Comparative Biochemical Characterization of a Human IgM Produced in Both Ascites and In vitro Cell Culture," Biotechnology, 4:512-515 (1993).
Morrison et al., "Chimeric human antibody molecules: Mouse antigen-binding domains with human constant region domains," Proc. Natl. Acad. Sci. USA, 81:6851-55 (1984).
Nifong et al., "Separation of IgG and IgM from albumin in citrated human plasma using electrodialysis and metal ion affinity precipitation," ASAIO J., 48:645-649 (2002).
Niles et al., "Polymer IgM Assembly and Secretion in Lymphoid and Nonlymphoid Cell Lines: Evidence that J Chain is Required for Pentamer IgM Synthesis," Proc. Natl. Acad. Sci. USA, 92:2884-88 (1995).
Page et al., "Purification of monoclonal antibodies," Methods Mol. Biol., 80:113-119 (1998).
Phillips et al., "Manufacture and quality control of CAMPATH-1 antibodies for clinical trials," Cytotherapy, 3:233-242 (2001).
Randall et al., "Direct Evidence That J Chain Regulates the Polymeric Structure of IgM in Antibody-secreting B Cells," J. Biol. Chem., 267:18002-07 (1992).
Randall et al., "J Chain Synthesis and Secretion of Hexameric IgM is Differentially Regulated by Lipopolysaccharide and Interleukin 5," Proc. Natl. Acad. Sci. USA, 89:962-966 (1992).
Sharma et al., "Study of IgM Aggregation in Serum of Patients with Macroglobulinemia," Clin. Chem. Lab. Med., 38:759-764 (2000).
Shitara et al., "Immunoglobulin Class Switch of Anti-Ganglioside Monoclonal Antibody from IgM to IgG," J. Immunol. Methods, 169:83-92 (1994).
Sorensen et al., "Structural Requirements for Incorporation of J Chain into Human IgM and IgA," Int. Immunol., 12:19-27 (2000).
Steinbuch et al., "Preparation of an IgM and IgA enriched fraction for clinical use," Prep. Biochem., 3:363-373 (1973).
Stocks et al., "Production and Isolation of Large Quantities of Monoclonal Antibody Using Serum-Free Medium and Fast Protein Liquid Chromatography," Hybridoma, 8:241-247 (1989).
Stoll et al., "Effects of culture conditions on the production and quality of monoclonal IgA," Enzyme Microb. Technol., 21:203-211 (1997).
Tachibana, "Gene expression of joining chain in murine peritoneal B-1 cells," Nihon Univ. Dent. J., 76:425-433 (2002) (English abstract included).
Wood et al., "High Level Synthesis of Immunoglobulins in Chinese Hamster Ovary Cells," J. Immunol., 145:3011-16 (1990).
Youd et al., "Synergistic roles of IgM and complement in antigen trapping and follicular localization," Eur. J. Immunol., 32:2328-37 (2002).
USPTO Restriction Requirement in U.S. Appl. No. 10/564,665, dated Jul. 9, 2008, 7 pages.
Fish & Richardson P.C., Response to Restriction Requirement dated Jul. 9, 2008, in U.S. Appl. No. 10/564,665, filed Aug. 8, 2008, 1 page.
USPTO Restriction Requirement in U.S. Appl. No. 10/564,665, dated Nov. 12, 2008, 6 pages.
Fish & Richardson P.C., Response to Restriction Requirement dated Nov. 12, 2008, in U.S. Appl. No. 10/564,665, filed Jan. 9, 2009, 1 page.
USPTO Non-Final Office Action in U.S. Appl. No. 10/564,665, dated Apr. 20, 2009, 16 pages.

Fish & Richardson P.C., Amendment in Reply to Action dated Apr. 20, 2009 in U.S. Appl. No. 10/564,665, filed Oct. 19, 2009, 6 pages.

USPTO Notice of Allowance in U.S. Appl. No. 10/564,665, dated Dec. 4, 2009, 11 pages.

International Search Report for App. Ser. No. PCT/JP2004/010444, mailed Oct. 26, 2004, 4 pages.

International Preliminary Report on Patentability for App. Ser. No. PCT/JP2004/010444, dated Jun. 3, 2005, 5 pages.

USPTO Non-Final Office Action in U.S. Appl. No. 10/574,827, dated Mar. 12, 2008, 11 pages.

Fish & Richardson P.C., Amendment in Reply to Action dated Mar. 12, 2008 in U.S. Appl. No. 10/574,827, filed Sep. 11, 2008, 9 pages.

USPTO Non-Final Office Action in U.S. Appl. No. 10/574,827, dated Dec. 19, 2008, 7 pages.

Fish & Richardson P.C., Amendment in Reply to Action dated Dec. 19, 2008 in U.S. Appl. No. 10/574,827, filed Jun. 18, 2009, 5 pages.

USPTO Non-Final Office Action in U.S. Appl. No. 10/574,827, dated Oct. 22, 2009, 8 pages.

Fish & Richardson P.C., Amendment in Reply to Action dated Oct. 22, 2009 in U.S. Appl. No. 10/574,827, filed Jan. 21, 2010, 9 pages.

International Search Report for App. Ser. No. PCT/JP2004/014919, mailed Dec. 7, 2004, 4 pages.

International Preliminary Report on Patentability for App. Ser. No. PCT/JP2004/014919, dated Sep. 12, 2005, 14 pages.

European Search Report for App. Ser. No. EP 04 79 2188, dated Sep. 21, 2009, 4 pages.

USPTO Restriction Requirement in U.S. Appl. No. 10/575,192, dated Apr. 15, 2008, 7 pages.

Fish & Richardson P.C., Response to Restriction Requirement dated Apr. 15, 2008 in U.S. Appl. No. 10/575,192, filed Sep. 12, 2008, 1 page.

USPTO Non-Final Office Action in U.S. Appl. No. 10/575,192, dated Jan. 26, 2009, 11 pages.

International Search Report for App. Ser. No. PCT/JP2004/014935, mailed Jan. 25, 2005, 4 pages.

International Preliminary Report on Patentability for App. Ser. No. PCT/JP2004/014935, 14 pages.

European Search Report for App. U.S. Appl. No. EP 04 79 2204, mailed Jul. 11, 2007, 3 pages.

* cited by examiner

ANTI-GANGLIOSIDE ANTIBODIES AND COMPOSITIONS

CROSS-REFERENCE TO RELATED APPLICATIONS

This application is a divisional application of U.S. patent application Ser. No. 10/564,665, filed Sep. 21, 2006, now U.S. Pat. No. 7,709,615, which is a National Stage of International Application No. PCT/JP2004/010444, filed Jul. 15, 2004, which claims the benefit of U.S. Patent Application Ser. No. 60/487,333, filed on Jul. 15, 2003. The contents of these prior applications are hereby incorporated by reference in their entireties.

TECHNICAL FIELD

The present invention relates to the production of IgM using genetic engineering technology.

BACKGROUND ART

In many species of higher animals, immunoglobulins (Ig) can be divided into five different classes: IgG, IgA, IgM, IgD, and IgE. These classes are different in size, charge, amino acid composition, sugar content, and the like. Among these classes, IgM makes up approximately 10% of whole plasma immunoglobulin. IgM is a major component of early-stage antibodies produced against cell membrane antigens that are of complex antigenicity, infectious microorganisms, and soluble antigens.

In general, human IgM has a pentamer structure in vivo. The five subunits, which constitute the pentamer structure of IgM, have a four-chain structure similar to IgG. The μ chain, the H (heavy) chain of IgM, is different from the γ chain, the H chain of IgG, with respect to the amino acid sequences, and additionally, they are different as follows:

The μ chain has one more domain in its constant region than the γ chain

The μ chain has four more oligosaccharide chains than the γ chain.

IgM has a polypeptide chain called J chain, which is not found in IgG. The J chain is considered to facilitate polymerization of μ chains before IgM is secreted from antibody-producing cells.

In recent years, advances in monoclonal antibody technology and recombinant DNA technology have enabled mass production of pure immunoglobulin Moreover, genetic engineering technology has allowed the production of chimeric and humanized antibodies. A chimeric antibody is an antibody which has a structure where a variable region has been changed to another variable region of a different species origin. For example, a "chimeric antibody" which has a variable region of a non-human animal species and a constant region of a human antibody is known (Reference 1/Proc. Natl. Acad. Sci. U.S.A, (1984) 81:6851). A humanized antibody made by transplanting complementarity determining regions (CDRs) from an animal species into human immunoglobulin is also known (Reference 2/Nature (1986) 321:521).

The anti-CD20 human chimeric antibody, Rituxan® (IDEC), and the anti-HER2/neu humanized antibody, Herceptin® (Genentech), are specific examples of anti-tumor antibodies. These antibodies have already passed clinical trials and have been approved for distribution. Antibody-dependent cellular mediated cytotoxicity (hereinafter referred to as ADCC activity) and complement-dependent cytotoxicity (hereinafter referred to as CDC activity) are known as effector functions of IgG and IgM. Since IgM has a CDC activity higher than that of IgG, it can be used as an anti-tumor antibody with the CDC activity as a main drug activity. However, unlike IgG, IgM forms a polymer as mentioned above. For this reason, the industrial scale production of recombinant IgM has been considered to be difficult.

Several production systems for IgM recombinants using non-lymphoid cells have been reported. For example, introducing the genes of IgM H and L (light) chains into C6 glioma cells, CHO cells, or HeLa cells successfully resulted in the formation of polymer; however, the yield from the CHO cells was very low (Reference 3/EMBO J. (1987) 9; 2753) (Patent document 1/WO89/01975). Moreover, IgM-producing CHO cell lines were obtained by incorporating IgM H and L chains into separate expression vectors and co-expressing them (Reference 4/J. Immunol. (1990) 145; 3011) (Reference 5/Human Antibodies (1997) 8; 137). These reports also showed that the recombinant IgM produced by the CHO cells formed a polymer, but they failed to reveal a ratio of pentamer and hexamer or the like.

The main reason that a polymeric structure of IgM recombinant has not been developed is that no analytical technique has been established. Specifically, the polymeric structure of IgM cannot be correctly analyzed using known analytical methods for immunoglobulin. For example, gel electrophoresis, such as SDS-PAGE, is known as a technique for separating and identifying proteins. However, the IgM macromolecule has a molecular weight of approximately one million. It is therefore difficult to quantitatively analyze the polymeric structure (pentamer and hexamer) using conventional means.

In a reported technique for analyzing the IgM polymeric structure, non-reducing SDS-PAGE was performed using RI-labeled IgM (Reference 6/J. Immunol. (1994) 152; 1206). However, to develop IgM as a drug, it is necessary to develop a technique with which the polymeric structure of IgM can be analyzed in manufacturing process. Specifically, analysis of the polymeric structure of IgM is required in all the steps of manufacturing, including selection of producing cells, monitoring of cell culture, purification, primary drug manufacturing, and pharmaceutical preparation. The use of RI, however, is not practical for assessment of all these steps.

[Reference 1] Proc. Natl. Acad. Sci. U.S.A, (1984) 81:6851
[Reference 2] Nature (1986) 321:521
[Reference 3] EMBO J. (1987) 9; 2753
[Reference 4] J. Immunol. (1990) 145; 3011
[Reference 5] Human Antibodies (1997) 8; 137
[Reference 6] J. Immunol. (1994) 152; 1206
[Patent document 1] WO89/01975

DISCLOSURE OF THE INVENTION

An objective of the present invention is to provide cells that have a high IgM production capability. Another objective of the present invention is to provide techniques for preparing IgM that has pentamer or hexamer structure. A further objective of the present invention is to provide methods for analyzing the IgM polymers or aggregates.

Many of previous studies for IgM have used lymphoid cells, such as myeloma, hybridoma, and B lymphoma cell lines. It has been confirmed that when a J chain gene is introduced into B cell lines at various differentiation stages, IgM secreted by the cells that don't express J chain forms a hexamer while IgM from cells that express J chain forms a pentamer (Proc. Natl. Acad. Sci. U.S.A, (1995) 92: 2884). Comparisons between pentamer and hexamer components fractionated from IgM secreted by a B lymphoma cell line and hybridoma cell line have indicated that the hexamer component has a higher CDC activity than the pentamer (Eur. J. Immunol., (1990) 20: 1971) (J. Immunol. (1998) 160; 5979). Thus, the polymerization of IgM is considered to be important in relation to CDC activity. It is difficult, however, to obtain a large amount of IgM pentamer or hexamer component from these lymphoid cell lines.

Gene recombination techniques are often employed to obtain a large amount of proteins which are difficult to acquire. For IgM, however, no established techniques enable the construction of polymeric structure in recombinants. Thus, the present inventors conducted exhaustive studies to establish techniques for producing cells which can yield a large amount of IgM as well as IgM having a polymeric structure.

As a result, the present inventors discovered that the pentamer IgM can be obtained by inserting genes encoding the H, L, and J chains into an appropriate vector and introducing it into a host cell. The present inventors also revealed that when no J chain expresses in the transformed cell, IgM mainly forms a hexamer. Furthermore, the present inventors confirmed that the yield of IgM by the cell is very high, and thus completed the present invention. Specifically, the present invention relates to the following IgM-producing cells, methods for producing IgM, and IgM polymers which can be obtained by means of these cells or methods. The present invention also provides methods for analyzing the IgM polymers or IgM aggregates.

[1] A transformed cell producing IgM of 100 mg/L or more.
[2] A transformed cell producing IgM of 35 pg/cell/day or more.
[3] The transformed cell of [1] or [2], which is a eukaryotic cell.
[4] The transformed cell of [1] or [2], which is a prokaryotic cell.
[5] The transformed cell of [3], which is a mammalian cell.
[6] The transformed cell of any one of [1] to [5], which is an established cell line.
[7] The transformed cell of [6], which is a non-lymphoid cell line.
[8] The transformed cell of [7], which is a CHO cell line.
[9] An expression vector comprising both (1) a nucleotide sequence encoding an IgM H chain and (2) a nucleotide sequence encoding an IgM L chain in the same vector, or a gene fragment comprising the genes (1) and (2).
[10] An expression vector comprising (1) a nucleotide sequence encoding an IgM H chain, (2) a nucleotide sequence encoding an IgM L chain, and (3) a nucleotide sequence encoding an IgM J chain in the same vector, or a gene fragment comprising the genes (1), (2), and (3).
[11] The expression vector or gene fragment of [9] or [10], wherein IgM secretion is controlled by a transcriptional regulatory sequence.
[12] The expression vector or gene fragment of [11], wherein the transcriptional regulatory sequence is selected from the group consisting of:
 major late promoter of adenovirus 2;
 early promoter of simian virus 40;
 mouse mammary tumor virus (MMTV)-LTR promoter;
 thymidine kinase promoter of herpes simplex virus;
 cytomegalovirus promoter;
 polypeptide chain elongation factor 1α promoter;
 bovine growth hormone promoter;
 β actin gene promoter; and
 CAG promoter.
[13] The expression vector or gene fragment of [12], wherein the transcriptional regulatory sequence is selected from the group consisting of:
 early promoter of simian virus 40;
 cytomegalovirus promoter;
 polypeptide chain elongation factor 1α promoter; and
 CAG promoter.
[14] A transformed cell transformed by the vector or gene fragment of any one of [9] to [13].
[15] The transformed cell of [14], which is selected from the transformed cell of any one of [1] to [8].
[16] The transformed cell of [14] or [15], wherein the expression vector or gene fragment comprises a nucleotide sequence encoding a J chain.
[17] The transformed cell of any one of [14] to [16], wherein the vector or gene fragment comprises a nucleotide sequence encoding an IgM J chain and the cell produces pentamer IgM with a content of 60% or more.
[18] The transformed cell of [17], which produces pentamer IgM with a content of 80% or more.
[19] The transformed cell of [14] or [15], wherein the vector or gene fragment comprises no nucleotide sequence encoding an IgM J chain and the cell produces hexamer IgM with a content of 50% or more.
[20] The transformed cell of [19], which produces hexamer IgM with a content of 80% or more.
[21] The transformed cell of any one of [14] to [16], wherein the vector or gene fragment comprises a nucleotide sequence encoding an IgM J chain and the cell produces IgM for which the ratio of the produced pentamer and hexamer (pentamer/hexamer ratio) is 1.5 or more.
[22] The transformed cell of [14] or [15], wherein the vector or gene fragment comprises no nucleotide sequence encoding an IgM J chain and the cell produces IgM for which the ratio of the produced hexamer and pentamer (hexamer/pentamer ratio) is 1.5 or more.
[23] The transformed cell of [14] or [15], wherein the expression vector or gene fragment comprising a gene encoding IgM H and L chains comprises no nucleotide sequence encoding a J chain and the nucleotide sequence encoding the J chain has been expressively introduced by co-transfection.
[24] A method for producing an IgM, comprising a step of culturing the cell of any one of [1] to [8] and [14] to [23] and then collecting the IgM.
[25] A method for producing a substantially pure IgM, comprising a step of purifying an IgM from a culture supernatant obtained from culture of the cell of any one of [1] to [8] and [14] to [23].
[26] An IgM obtained by the method of [24].
[27] A substantially pure IgM obtained by the method of [25].
[28] The IgM of [26] or [27], which is a human, mouse, human chimeric, or humanized antibody.
[29] The IgM of any one of [26] to [28], which is a substantially pure pentamer or hexamer.
[30] A substantially pure pentamer or hexamer IgM comprising a sugar chain added by a CHO cell.
[31] The IgM of any one of [26] to [30], which is an anti-sugar chain antibody.
[32] The IgM of [31], which is an anti-ganglioside antibody.
[33] The IgM of [32], which is an anti-GM2 or GM3 antibody.
[34] An isolated polynucleotide comprising the nucleotide sequence of SEQ ID NO: 1 or a nucleotide sequence encoding the amino acid sequence of SEQ ID NO: 2.
[35] An isolated polynucleotide comprising the nucleotide sequence of SEQ ID NO: 3 or a nucleotide sequence encoding the amino acid sequence of SEQ ID NO: 4.
[36] An isolated protein comprising an amino acid sequence encoded by the polynucleotide of [34].

[37] An isolated protein comprising an amino acid sequence encoded by the polynucleotide of [35].
[38] An IgM comprising the protein of [36] and the protein of [37] as constituent units.
[39] The IgM of [38], further comprising an IgM J chain.
[40] The IgM of [39], which is a pentamer.
[41] An isolated polynucleotide comprising the nucleotide sequence of SEQ ID NO: 19 or a nucleotide sequence encoding the amino acid sequence of SEQ ID NO: 20.
[42] An isolated polynucleotide comprising the nucleotide sequence of SEQ ID NO: 21 or a nucleotide sequence encoding the amino acid sequence of SEQ ID NO: 22.
[43] An isolated protein comprising an amino acid sequence encoded by the polynucleotide of [41].
[44] An isolated protein comprising an amino acid sequence encoded by the polynucleotide of [42].
[45] An IgM comprising the protein of [43] and the protein of [44] as constituent units.
[46] The IgM of [45], further comprising an IgM J chain.
[47] The IgM of [46], which is a pentamer.
[48] A pharmaceutical composition comprising the IgM of any one of [26] to [33], [38], and [45].
[49] A pharmaceutical composition comprising 80% or more pentamer IgM.
[50] A pharmaceutical composition comprising 50% or more hexamer IgM.
[51] The pharmaceutical composition of [50], comprising 80% or more hexamer IgM.
[52] A pharmaceutical composition comprising an IgM for which pentamer/hexamer ratio is 1.5 or more.
[53] A pharmaceutical composition comprising an IgM for which hexamer/pentamer ratio is 1.5 or more.
[54] A method for analyzing an IgM polymer, comprising a step of separating an IgM by SDS-polyacrylamide gel electrophoresis using as a carrier polyacrylamide gel satisfying at least one condition selected from the group consisting of:
   a) a polyacrylamide gel polymerized at a high temperature;
   b) a polyacrylamide gel containing a high concentration of ammonium persulfate and glycerol; and
   c) a polyacrylamide gel homogenized by stirring and degassed prior to polymerization.
[55] The method of [54], wherein the temperature in condition a) is 37° C. or higher.
[56] The method of [54], wherein the concentration of ammonium persulfate in condition b) is 0.25% or more.
[57] The method of [54], wherein the polyacrylamide gel satisfies at lease two conditions selected from the group consisting of conditions a) to c).
[58] The method of [54], wherein the polyacrylamide gel satisfies all the conditions a) to c).
[59] The method of [54], wherein a buffer for electrophoresis is a Tris-acetate SDS electrophoresis buffer.
[60] The method of [54], wherein the IgM polymer is an IgM pentamer and/or hexamer.
[61] The method of [54], wherein the method comprises analyzing an IgM aggregate.
[62] The method of [54], wherein the method is free from use of R1.
[63] The method of [54], comprising a step of quantifying the IgM polymer separated after electrophoresis.
[64] An electrophoresis gel for separating an IgM polymer by SDS-polyacrylamide gel electrophoresis, comprising a polyacrylamide gel satisfying at least one condition selected from the group consisting of:
   a) a polyacrylamide gel polymerized at a high temperature;
   b) a polyacrylamide gel containing a high concentration of ammonium persulfate and glycerol; and
   c) a polyacrylamide gel homogenized by stirring and degassed prior to polymerization.
[65] A method for producing an electrophoresis gel for separating an IgM polymer by SDS-polyacrylamide gel electrophoresis, comprising at least one step selected from the group consisting of:
   a) polymerizing an acrylamide at a high temperature;
   b) adding a high concentration of ammonium persulfate to an acrylamide, and
   c) homogenizing an acrylamide by stirring and degassed prior to polymerization.

The present invention provides transformed cells producing 100 mg/L or more of IgM. As used herein, the term "transformed cells" refers to cells that expressively carry foreign IgM genes. The phrase "producing 100 mg/L or more of IgM" means that the IgM-producing cells can accumulate 100 mg or more IgM in 1 L of culture supernatant thereof. The IgM yield in the culture can be measured by ELISA or the like. According to the present invention, the amount of accumulated IgM is usually 100 mg/L or more, preferably 120 mg/L or more, and more preferably 150 to 300 mg/L. Since IgM has been considered to be difficult to produce in a large amount because of its polymeric structure, it can be said that the yield achieved by the transformed cells of the present invention is an extremely high level.

The yield of a monoclonal antibody produced by a hybridoma cell line established by cell fusion technique is usually several mg to several tens mg/L, even in the case of IgG for which a high yield can be expected. In other words, the transformed cells of the present invention produce a far larger amount of IgM than the standard yield of monoclonal antibody produced by hybridoma cell line.

As used herein, IgM refers to an immunoglobulin that has a pentamer or hexamer structure and a μ chain constant region as the H chain constant region. In the context of the present invention, the origin of the IgM variable region is not limited. Therefore, it may include an IgG-derived variable region or its partial structure in addition to a variable region from a μ chain. The partial structure of the variable region may include frameworks and CDRs. According to the present invention, IgM means an expression product of a foreign IgM gene which has been introduced into transformed cells.

Furthermore, animal species from which the constant region constituting IgM of the present invention derives are not limited. In other words, the IgM of the present invention includes an IgM constant region derived from any animal species that has IgM-type immunoglobulin. When IgM is used for in vivo administration, it is preferable that at least constant region of the IgM is derived from the same species as the subject. Therefore, to administer the IgM to a human, at least constant region is preferably derived from a human. IgM composed of human-derived constant regions and nonhuman species-derived variable regions or variable regions from another human individual, is called a chimeric antibody.

When administering to humans, it is preferred that the IgM have constant regions as well as frameworks of variable regions derived from human. An antibody in which the framework structure of variable regions is maintained and only CDRs have been changed to those of another animal species is called a humanized antibody.

The present invention also provides transformed cells producing IgM of 35 pg/cell/day or more. The IgM yield/cell/day from a preferred transformed cell of the present invention is generally 35 pg or more, preferably 40 pg or more. The IgM yield/cell may be determined based on the amount of IgM accumulated in the culture and the number of transformed cells in the culture. When the transformed cells are cloned cells, the IgM yield/cell thus determined can be assumed to be a common characteristic shared equally by all the cells of the cell population.

IgM is usually secreted into a culture supernatant after being expressed and configured in cells. However, IgM may remain within the cells provided IgM having its functional conformation can be collected by homogenizing the cells or the like. If the collected IgM molecules can recover the functional conformation through any process, they don't need to exhibit an IgM activity in the culture supernatant.

The transformed cells having a high IgM production capacity provided by the present invention can be obtained by transforming an appropriate host cell with a vector or a gene fragment in which the genes of the H composing the μ chain and L chains have been expressibly placed. The host cell from which the transformed cell of the present invention can be obtained and methods for transforming the cell are described in detail below.

First, DNA encoding the desired H and L chains is incorporated into an expression vector. Another gene encoding the J chain may be combined with the DNA for incorporation into the expression vector. These genes are incorporated into the expression vector so that they will be expressed under the control of expressional regulatory regions.

Methods for obtaining the genes (IgM genes) encoding the H, L, and J chains of IgM are known. Hereinafter, the term "IgM gene" means any of the genes encoding the H, L, and J chains composing IgM.

The gene encoding the human J chain has been cloned and its structure has been revealed (GenBank Accession No. M12759, Max & Korsmeyer, J. Exp. Med. (1985) 161:832-849). Based on information of the revealed nucleotide sequence, the gene encoding the J chain can be obtained using mRNA from IgM-producing cells as template.

For example, primers J-f1 and J-r1 for amplifying the J chain described in Examples can be used to amplify DNA encoding the J chain. The nucleotide sequence of the J chain-encoding cDNA isolated in Examples is shown in SEQ ID NO: 5 and the amino acid sequence encoded by the nucleotide sequence is shown in SEQ ID NO: 6.

The genes encoding the H and L chains are described below. Generally, when obtaining immunoglobulin genes, it is important to obtain nucleotide sequences encoding a region covering the variable region. The structure of the immunoglobulin constant region is conserved. Therefore, it is believed that once an immunoglobulin gene is cloned, an immunoglobulin having a target antigen-binding activity can be reconstituted by recombining its variable region. Thus, in general, nucleotide sequences encoding whole immunoglobulins are constructed by obtaining genes of variable regions or CDRs and transplanting them into previously cloned constant regions or frameworks. The structure of the constant regions of the H or L chains composing IgM has already been determined μ chain constant region: Dorai & Gillies, Nucleic Acids Res. (1989) 17:6412

κ chain constant region: Hieter et al., Cell (1980) 22:197-207

γ chain constant region: Hieter et al., Nature (1981) 294:536-540

The IgM of the present invention also includes IgM whose constant region is altered. For example, the constant region of the μ, H or L chain composing IgM may be altered to improve its CDC activity. An IgM molecule can be rendered ADCC activity by combining with Fc region of IgG.

In the present invention, the origin of the gene encoding the variable region is not limited. For example, the variable region gene can be amplified from IgM-producing cells by PCR technique. Primers for amplifying the variable region gene by PCR are known (Ivanovzki et al., Blood (1998) 91:2433-2442). The variable region gene can be isolated from a phage antibody library (Clackson et al., Nature (1991) 352:624-628; Marks et al., J. Mol. Biol. (1991) 222:581-597). Furthermore, a variable region gene of an immunoglobulin other than IgM, such as IgG, can be joined to the IgM constant region.

Any immunoglobulin-producing cell can be used as the IgM-producing cells or other immunoglobulin-producing cells in order to obtain the variable region genes. For example, a variable region gene of human IgM, human IgG, or the like can be obtained from B cells collected from human peripheral blood. Specifically, it is preferable to obtain a variable region gene after preparing fusion cells of human IgM-or human IgG-producing B cells with myeloma cells or transforming human IgM-or IgG-producing B cells with Epstein-Ban virus for immortalization followed by screening for cells producing IgM against a target antigen. A variable region gene of IgM or IgG can also be obtained from B cells or immunocompetent cells obtained from an animal immunized with a target antigen.

Furthermore, a full-length nucleotide sequence encoding IgM can be obtained from the mRNA of IgM-producing cells. First, a portion encoding the constant region whose structure has been previously revealed may be amplified by PCR. Next, a portion encoding the variable region may be obtained by a technique for determining a 5'-side unknown nucleotide sequence. Techniques for amplifying unknown nucleotide sequences based on a known nucleotide sequence are known. For example, a 5'-side unknown nucleotide sequence can be obtained by 5'RACE.

Alternatively, when a previously cloned IgM gene is available, the gene can be used to construct a vector or a gene fragment mentioned below as it is or after being amplified if necessary.

For example, the nucleotide sequence of L612, an IgM antibody to ganglioside GM3, has been revealed (Cancer Research 1993; 53:5244-5250). Moreover, the nucleotide sequence of L55, an IgM antibody to ganglioside GM2, is also known (Immunogenetics 1998; 48:73-75).

The IgM gene used in the present invention may be altered to generate an IgM antibody variant. As used herein, the term "antibody variant" refers to an amino acid sequence variant of an antibody in which one or more amino acids have been altered. Any amino acid variant is included in "antibody variant" in the context of the present invention so long as it has the same binding specificity as the original antibody, regardless of how it has been altered. Such a variant has a sequence homology or similarity of less than 100% to an amino acid sequence that has a sequence homology or similarity of at least 75%, preferably at least 80%, more preferably at least 85%, even more preferably at least 90%, and most preferably at least 95% to the amino acid sequence of the antibody H or L chain variable domain.

For example, pentamer/hexamer structure conversion was confirmed for a variant having a Cys insertion in the IgM H chain (Davis, et al. EMBO J. (1989) 8, 2519-2526). It was also confirmed that introducing a deletion or mutation into four regions (Cμ1, Cμ2, Cμ3, and Cμ4) of the IgM H chain resulted in changes in J chain incorporation and pentamer/ hexamer structure. Based on this knowledge, genes encoding IgM variants capable of composing the target pentamer or hexamer can be obtained.

An IgM antibody of the present invention may also have a modified sugar chain.

As expressional regulatory regions, for example, enhancers and promoters can be used in the present invention. Such an expression vector can be introduced into host cells to express IgM.

Alternatively, a gene fragment containing these genes can be introduced into host cells to obtain transformed cells of the present invention. For example, a gene fragment containing an expression cassette composed of expressional regulatory regions and structural genes can be introduced into the genome of the host cell by homologous recombination. The host cell carrying the gene fragment can express the structural genes.

To obtain the transformed cells of the present invention, an appropriate combination of a host cell and an expression vector or a gene fragment may be used. Both prokaryotic and eukaryotic cells may be used as host cells. Exemplary prokaryotic cells include, for example, *Escherichia coli* (*E. coli*) and *Bacillus subtilis*. For eukaryotic cells, systems for expressing various kinds of foreign genes have been put into practice in mammalian cells, plant cells, insect cells, yeast cells, and the like.

Preferred host cells for obtaining the transformed cells of the present invention include mammalian cells and insect cells. As mentioned above, the μ chain has several sugar chain binding sites. To obtain IgM whose structure is more close to that of natural IgM, sugar chains can be attached to these sugar chain binding sites. The IgM having the μ chain resembling the natural one is expected to have a higher IgM activity. The IgM activity includes, for example, CDC activity and capability of forming a polymer or aggregate. The IgM structure close to that of the natural molecule contributes to improvements in efficacy and safety of IgM, because natural IgM structure is most unlikely to be affected by immunological elimination mechanism of a recipient.

To express IgM with sugar chains, the use of eukaryotic cells is advantageous. In particular, mammalian cells are the preferred host cells. More specifically, non-lymphoid mammalian cells are easy to culture and preferable as host cells because most do not express the J chain (Cattaneo & Neuberger, EMBO J. (1987) 6:2753-2758, Davis et al., J. Exp. Med. (1988) 18:1001-1008). The non-lymphoid cell lines include CHO, COS, and NIH3T3 cells. In these animal cells, sugar chain additions similar to those arising in natural IgM are expected to take place. In particular, CHO cells are the preferred host cells because they can provide a high level of IgM expression and an addition of sugar chains closest to that which occurs in nature.

The transformed cells of the present invention can be obtained by introducing and expressing nucleotide sequences (IgM genes) encoding the IgM H and L chains, and if necessary, the J chain, in these host cells. Expression vectors for introducing and expressing foreign genes into these host cells are known in the art.

When eukaryotic cells are used as host cells, the host-vector systems listed below, for example, can be used in the present invention.

For example, pCXN (Niwa et al., Gene 1991; 108:193-200), pcDNA3 (Invitrogen), pEGF-BOS (Nucleic Acids. Res. 1990, 18(17), p 5322), pEF, and pCDM8 are known as expression vectors derived from mammals. Expression vectors derived from animal virus can also be used to transform mammalian cells. The virus-derived expression vectors include pHSV, pMV, and pAdexLcw. paPneo, an expression vector derived from a retrovirus, is also useful for transformation of animal cells.

In addition, pBacPAK8 is commercially available as an expression vector for insect cells ("Bac-to-BAC baculovairus expression system", GIBCO BRL). The expression vectors for plant cells include, for example, pMH1 and pMH2. The expression vectors for yeasts include, for example, "*Pichia* Expression Kit" (Invitrogen), pNV11, and SP-Q01.

For expression in animal cells such as CHO, COS, and NIH3T3 cells, the IgM genes are arranged to express under the control of expressional regulatory regions. The expressional regulatory regions include enhancers and promoters. For example, the promoters useful for mammalian cells include:

Major late promoter of adenovirus 2;
Early promoter of simian virus 40;
Thymidine kinase promoter of herpes simplex virus;
Cytomegalovirus promoter;
Polypeptide chain elongation factor 1α promoter (Mizushima et al., Nucleic Acids Res. (1990) 18, 5322);
Bovine growth hormone promoter;
β actin gene promoter;
CAG promoter;
SV40 promoter (Mulligan et al., Nature (1979) 277, 108); and
Mouse mammary tumor virus (MMTV)-LTR promoter.

Among these promoters, the preferred promoters are as follows. These promoters are expected to exhibit a high expression induction activity in mammalian cells.

Early promoter of simian virus 40,
Cytomegalovirus promoter,
Polypeptide chain elongation factor 1α promoter, and
CAG promoter The expression vectors may further contain a selective marker to facilitate the selection of transformed cells. A drug resistant gene, such as that to neomycin or G418, is generally used as a selective marker. Vectors having such a characteristic include, for example, pMAM, pDR2, pBK-RSV, pBK-CMV, pOPRSV, and pOP13.

Techniques for stable expression of an introduced gene in transformed cells and amplification of the number of gene copies in the cells are known. For example, by transforming CHO cells deficient in a nucleic acid synthetic pathway with a vector carrying a DHFR gene which complements the deficiency, gene expression can be amplified with methotrexate (MTX). The DHFR gene includes, for example, pCHOI.

Furthermore, transient gene expression can be achieved by transforming COS cells having a gene for expressing SV40 T antigen on its chromosome with a vector having SV40 replication origin. Vectors having SV40 replication origin include, for example, pcD. For the origin of replication, those derived from polyomavirus, adenovirus, bovine papilloma virus (BPV), and the like may be used.

To amplify the number of gene copies in the transformed cell, the expression vector may contain an aminoglycoside transferase (APH) gene, thymidine kinase (TK) gene, *E. coli* xanthine guanine phosphoribosyltransferase (Ecogpt) gene, dihydrofolate reductase (dhfr) gene, or the like.

In addition to eukaryotic cells, prokaryotic expression systems can also be used in the present invention. Expression vectors for *E. coli* include, for example, the M13 series vectors, pUC series vectors, pBR322, pBluescript, and pCR-Script. Expression vectors derived from *Bacillus subtilis* include pPL608 and pKTHSO. When *E. coli*, such as JM109, DH5α, HB101, or XL1-Blue, is used as the host cell, a promoter capable of efficiently expressing in *E. coli* should also be used. Such promoters include, for example, lacZ promoter (Ward et al., Nature (1989) 341, 544-546; FASEB J. (1992) 6, 2422-2427), araB promoter (Better et al., Science (1988) 240, 1041-1043), and T7 promoter. Such vectors include, for example, pGEX-5X-1 (Pharmacia), "QIAexpress system" (Qiagen), pEGFP, and pET as well as the vectors mentioned above. In the case of pET, the host cell is preferably BL21, which expresses T7 RNA polymerase.

The vector may contain a signal sequence for polypeptide secretion. To produce a polypeptide in *E. coli* periplasm, the pelB signal sequence (Lei, S. P. et al. J. Bacteriol. (1987) 169, 4379) may be used as the signal sequence for polypeptide secretion. The vector can be introduced into the host cell by, for example, the calcium chloride method or electroporation.

The present invention provides transformed cells into which a vector or gene fragment has been introduced. The host cells to receive the vector are not limited. For example, E. coli cells and various animal cells can be used. The transformed cells of the present invention can be used as, for example, a system for IgM production and expression. Systems for polypeptide preparation include both in vitro and in vivo production systems. The in vitro production systems include systems using a eukaryotic cell or a prokaryotic cell.

When using a eukaryotic cell, for example, an animal, plant, or fungal cell may be used as the host cell. As an animal cell line or a human cell line, the mammalian cell lines listed below are known, for example.

CHO (hamster ovarian cell, J. Exp. Med. (1995) 108, 945),
COS (monkey kidney cell, Miyazaki, et al., Gene (1989) 79, 269),
3T3 (mouse fibroblast),
PC12 (human plasmacytoma, Neumann, et al., EMBO J. (1982) 1, 841),
BHK (baby hamster kidney),
HeLa (human epithelial cell, Cattaneo, et al. EMBO J. (1987) 6, 2753),
C6 (human glioma cell, Cattaneo, et al. Eur. J. Biochem. (1983) 135, 285),
Vero (monkey kidney cell, Cytology (1991) 7, 165), and
Amphibian cells such as *Xenopus* oocyte (Valle, et al., Nature (1981) 291, 358-340).

In addition, insect cells, such as Sf9, Sf21, and Tn5, are known.

As CHO cells, in particular, dhfr-CHO cells which are DHFR gene-deficient (Proc. Natl. Acad. Sci. USA (1980) 77, 4216-4220) and CHO K-1 (Proc. Natl. Acad. Sci. USA (1968) 60, 1275) are preferred. When mass expression in animal cells is desired, CHO cells are particularly preferable. These cell lines are available from depositary institutions. Representative cell lines and their ATCC Accession Numbers are listed below.

CHO CCL-61, CRL-9096 BHK CRL-1632
COS CRL-1650, CRL-1651 HeLa CCL-2
3T3 CRL-1658 Vero CCL-81

The expression vector can be introduced into the host cell by any method. The methods for introducing the vector include, for example, those listed below:
Calcium phosphate method;
DEAE dextran method;
Method using cationic liposome DOTAP (Boehringer Mannheim);
Electroporation method; and
Lipofection.

As for the plant cell, for example, a *Nicotiana*-derived cell is known as a polypeptide producing system which may be cultured as callus. Recently, some studies have reported on polypeptide production in *Lemnaceae* and *Zea mays*. As for fungal cells, yeasts, for example, the genus *Saccharomyces* including *Saccharomyces cerevisiae*, and filamentous fungi, for example, the genus *Aspergillus* including *Aspergillus niger*, are known.

When a prokaryotic cell is used, a producing system using a bacterial cell may be employed. The bacterial cells include *E. coli*, such as JM109, DH5α, and HB101; *Bacillus subtilis* is also known.

By transforming these host cells with the expression vectors or gene fragments, the transformed cells capable of IgM production can be obtained. By selecting cells with high IgM production from among these transformed cells, the transformed cell of the present invention may be obtained.

For example, transformed cells may be cloned and each clone may be assessed for their IgM productivity. The productivity of IgM may be determined by culturing the transformed cells in an appropriate culture medium and measuring the IgM contained in the culture supernatant. To select the cell producing high-titer IgM having a desired reactivity, an immunoassay may be conducted using a target antigen. For example, the ELISA method, which uses a microtiter to which an antigen is attached, is preferable as a method for measuring whether the antigen-specific IgM has been successfully produced. To assess the cytotoxic activity of IgM, a complement receptor may be analyzed or the CDC activity of IgM may be assessed. For example, methods for measuring IgM and specific methods for determining the IgM yield/cell are shown in Example (1.6).

Furthermore, the present invention provides transformed cells producing pentamer or hexamer IgM. The present inventors revealed that IgM expresses as a pentamer when the IgM gene contained in the expression vector or gene fragment for transforming the host cell has a nucleotide sequence encoding the J chain. The inventors also showed that IgM expresses as a hexamer when the IgM gene has no nucleotide sequence encoding the J chain. Thus, this finding of the present invention enables the control of the IgM polymeric structure.

According to the preset invention, the nucleotide sequence encoding the J chain may be inserted into the same vector that carries the nucleotide sequences encoding the H and L chains. Alternatively, through co-transfection of the vector carrying the nucleotide sequence encoding the J chain and the vector carrying the nucleotide sequences encoding the H and L chains, they may be introduced into cells. In addition, the nucleotide sequences encoding the H, L, and J chains may individually be placed into separate vectors to co-transfect into the same cell.

By inserting the three genes into a single vector for transforming the host cell, differences in transformation efficiency or expression level among the vectors can be prevented. In other words, the expression vector carrying the three genes of the H, L, and J chains is preferable as a vector for obtaining the transformed cell of the present invention.

Specifically, the present invention relates to the transformed cells in which the vector or gene fragment has the nucleotide sequence encoding the IgM H, L, and J chains and which produce 60% or more content of pentamer IgM. The preferred transformed cells of the present invention produce 80% or more content of pentamer IgM. The percentage of the pentamer IgM in the produced IgM molecules may be determined by, for example, the method mentioned below (Example 4). According to the present invention, the ratio of pentamer and hexamer (pentamer/hexamer ratio) in total IgM is, for example, 1.5 or more, preferably 5 or more, and more preferably 10 or more.

The present invention also relates to the transformed cells in which the gene fragment or vector has the nucleotide sequences encoding the IgM H and L chains but no nucleotide sequence encoding the J chain, and which produce 50% or more content of hexamer IgM. According to the present invention, the preferred transformed cells produce 80% or more content of hexamer IgM. The percentage of hexamer IgM in the produced IgM molecules may be determined by, for example, the method mentioned below (Example 4). According to the present invention, the ratio of hexamer and pentamer (hexamer/pentamer ratio) in total IgM is, for example, 1.5 or more, preferably 5 or more, and more preferably 10 or more. It has been already reported that the hexamer IgM has a higher CDC activity than the pentamer. Thus, the method of the present invention, which can preferentially manufacture the hexamer IgM, is useful as a technique for manufacturing antibody drugs.

A major constituent of IgM found in vivo is the pentamer formed through the J chain The production of recombined IgM with high content of pentamer is useful because it provides an IgM closest to the natural molecule. The incorporation of the J chain almost completely prevents the production of other IgM molecules (monomer to tetramer and hexamer) than the pentamer (Wiersma et al., J. Immunol. (1998) 160: 5979-5989, Sørensen et al., Int Immunol. (2000) 12:19-27), and thus it allows the production of a purer pentamer recombinant IgM.

The transformed cells are cultured and then IgM can be obtained from the culture. Methods for culturing the transformed cells in vitro or in vivo are known. For example, animal cells may be cultured in an appropriate animal cell culture medium. Culture media such as DMEM, MEM, RPMI1640, and IMDM are known as the culture media for animal cells. These cells may be cultured in a medium with a serum supplement, such as fetal calf serum (FCS), or in serum-free culture media. Preferred pH for culture is about 6 to 8. The culture is usually conducted at about 30 to 40° C. for about 15 to 200 hours while the culture medium is replaced, aerated, or stirred, if necessary.

As in vitro culture methods, methods for culturing cells dispersed in the culture medium and for contacting cells with the culture medium through a semipermeable membrane are known. As an in vivo culture method, a method for inoculating cells into the abdominal cavity of a mouse is known.

The animal cells, such as CHO cells, transformed with the IgM expression vector secrete IgM into the culture supernatant. Accordingly, the culture supernatant may be collected to obtain the target IgM. IgM can be purified from the culture supernatant by a purification technique including gel filtration, ion exchange chromatography, and affinity chromatography (Antibodies: A Laboratory Manual. Ed Harlow and David Lane, Cold Spring Harbor Laboratory, 1988). The present invention provides a method for manufacturing a substantially pure IgM purified from the culture supernatant. As used herein, the term "substantially pure IgM" can be defined as IgM free from any other proteins derived from transformed cells and cultured media from which the IgM molecule is derived. For example, when the IgM molecules collected from the cell transformed with the human-derived IgM gene are free from any proteins other than the human-derived IgM protein, this IgM can be referred to as substantially pure IgM. Herein, it is preferable that the substantially pure IgM be substantially free from any other proteins derived from host cells or protein components of the culture solution used for culturing the host cells. The term "substantially free" means that the percentage of other protein components to total proteins is 20% or less, for example, 10% or less, preferably 5% or less, or 2% or less, and more preferably 1% or less.

The IgM or substantially pure IgM antibodies that can be obtained by means of these manufacturing methods are included in the present invention. Preferred IgM antibodies of the present invention are composed of 50% or more hexamer, 60% or more pentamer, or preferably 80% or more pentamer or hexamer IgM molecule. The IgM antibodies of the present invention composed of at least 50% or more hexamer or 60% or more pentamer are referred to as substantially pure pentamer or hexamer, respectively. According to the present invention, the content of the substantially pure pentamer or hexamer is more preferably, for example, 80% or more. The substantially pure IgM is useful as a pharmaceutical composition.

The animal species from which the IgM antibody of the present invention is derived are not limited. According to the present invention, for example, a human antibody or a mouse antibody may be obtained. As mentioned earlier, the IgM antibody of the present invention may be a chimeric antibody, having the constant and variable regions of which genes are derived from different species. The chimeric antibody includes a human (constant)-human (variable) chimeric antibody and a human (constant)-nonhuman animal (variable) chimeric antibody. A gene encoding the human-human chimeric antibody can be obtained by joining any variable region gene to a previously cloned human constant region gene. Furthermore, the present invention includes a humanized antibody. The humanized antibody can be obtained by expressing a gene in which CDRs of non-human animal origin have been incorporated between the frameworks of a human variable region gene.

Antigens recognized by the IgM antibody of the present invention are not limited. The IgM antibody has a strong cytotoxicity with CDC activity. Moreover, an IgM antibody with cell-killing activity has been reported (Yonehara et al., J. Exp. Med. (1989) 169:1747-1756). Therefore, the IgM antibody is useful for medical technologies wherein the therapeutic strategy focuses on cytotoxicity, for example, cancer treatment. For example, it is known that various sugar chain antigens can be used as cell surface markers for tumor cells. Thus, an IgM antibody recognizing the sugar chains is useful as an antibody drug targeting the cells. For example, it is known that a certain kind of ganglioside is useful as a target molecule for an antibody drug against tumor cells. Specifically, it has been confirmed that the antibody to ganglioside GM2, GD2, GD3, or GM3 has cytotoxic effects on several kinds of tumor cells. A preferred IgM of the present invention is exemplified by the IgM antibody to ganglioside GM2 or ganglioside GM3. These IgM antibodies can be produced by the method of the present invention.

Several antibodies recognizing ganglioside GM2 or GM3 have been reported. Herein, the anti-ganglioside GM2 or GM3 antibody is not limited to a specific origin. A known IgM antibody gene may be used or a new anti-IgM antibody gene may be obtained for application to the present invention. For example, the preferred variable regions of the anti-ganglioside GM2 and GM3 antibodies in the present invention are exemplified by the amino acid sequences of the SEQ ID NOs shown below. The nucleotide sequences of the DNAs encoding these amino acid sequences are indicated in parentheses.

Anti-Ganglioside GM2 Antibody (L55):
  H chain: SEQ ID NO: 20 (SEQ ID NO: 19)
  L chain: SEQ ID NO: 22 (SEQ ID NO: 21)
Anti-Ganglioside GM3 Antibody (L612):
  H chain: SEQ ID NO: 2 (SEQ ID NO: 1)
  L chain: SEQ ID NO: 4 (SEQ ID NO: 3)

The present invention also provides pharmaceutical compositions containing the IgM antibody as an active ingredient. In particular, the present invention provides an IgM comprising pentamer or hexamer at a larger amount than the other. Thus, the present invention provides pharmaceutical compositions enriched with IgM pentamer or hexamer. Specifically, the present invention provides pharmaceutical compositions in which the pentamer/hexamer ratio is, for example, 1.5 or more, preferably 5 or more, and more preferably 10 or more. The present invention also provides pharmaceutical compositions in which the hexamer/pentamer ratio is, for example, 1.5 or more, preferably 5 or more, and more preferably 10 or more.

For example, by administering a pharmaceutical agent containing anti-ganglioside GM2 or GM3 IgM antibody of the present invention as an active ingredient, cancer can be treated or prevented. Moreover, by administering a pharmaceutical agent containing the anti-ganglioside GM2 IgM antibody as an active ingredient, AIDS can be treated or prevented. The present invention also provides these therapeutic and preventive methods.

The pharmaceutical agent containing the anti-ganglioside GM2 or GM3 IgM antibody as an active ingredient can be administered by any route. The pharmaceutical agent may be orally or parenterally administered. Preferably, the agent is parenterally administered. Specifically, parenteral administration can be performed by, for example, injection, transnasal, transpulmonary, or transdermal administration. The injections may be systemically or locally administered by, for example, intravenous, intramuscular, intraperitoneal, or subcutaneous injection. Furthermore, they may be administered directly to an affected area of cancer.

In addition to directly administering to a patient the pharmaceutical agent containing the anti-ganglioside GM2 or GM3 IgM antibody as an active ingredient, the agent can be administered as a formulated preparation manufactured by a known pharmaceutical method. For example, the agent may be used as an injection in the form of a sterile solution or suspension with water or another pharmaceutically acceptable liquid. The agent may also be formulated by, for example, combining with an appropriate pharmacologically acceptable carrier or medium, specifically sterile water, physiological saline, emulsifying agent, suspending agent, surfactant, stabilizer, vehicle, preservative, or the like in a generally accepted unit dosage form required for pharmaceutical implementation. The amount of the active ingredient in these formulations can be adjusted to provide an appropriate dose within a prescribed range.

A sterile composition for injection can be formulated according to a conventional pharmaceutical implementation using a vehicle such as distilled water for injection. For example, physiological saline or isotonic solution containing glucose and/or other auxiliary agents may be used as an aqueous solution for injection. Specific auxiliary agents include D-sorbitol, D-mannose, D-mannitol, and sodium chloride. An appropriate solubilizing agent may be added to the pharmaceutical compositions. Preferred solubilizing agents include, for example, alcohol and non-ionic surfactant. Specific alcohol includes ethanol and polyalcohol, for example, propylene glycol and polyethylene glycol. Polysorbate 80™ HCO-50, for example, may be used as the non-ionic surfactant.

Oils, such as sesame oil and soybean oil, may be used with benzyl benzoate or benzyl alcohol as a solubilizing agent. The formulations may be prepared by combining with a buffer, for example, phosphate buffer or sodium acetate buffer; a soothing agent, for example, procaine hydrochloride; a stabilizer, for example, benzyl alcohol or phenol; and an antioxidant. The prepared injection solution is usually loaded into an appropriate ampoule.

An appropriate dosage may be selected depending on the age and condition of a patient. For example, a single dosage may be selected from a range of 0.0001 mg to 1,000 mg/kg body weight. For example, the dosage may be selected from a range of 0.001 to 100,000 mg/body. Therapeutic agents of the present invention, however, are not limited to these dosages.

The IgM antibody, once bound to a cell membrane or taken into the cell, has cytotoxic effects by itself or in the presence of a complement. The therapeutic effects of the antibody formulations of the present invention using the IgM antibody can further be improved by combining the antibody with various kinds of therapeutic components. Such therapeutic components include chemotherapeutic agents, such as doxorubicin, methotrexate, and taxol, heavy metals, radionuclides, and toxins such as *Pseudomonas* toxin. Methods for producing a conjugate with the therapeutic component and for using it for treatment are disclosed in U.S. Pat. Nos. 5,057,313 and 5,156,840. The therapeutic effects can be improved by combining the IgM antibody obtained according to the present invention with a chemotherapeutic agent or an antibody formulation which recognizes the same or a different kind of antigen.

Furthermore, the present invention provides a method for analyzing the IgM polymer, which comprises a step of separating the IgM by SDS-polyacrylamide gel electrophoresis using a polyacrylamide gel satisfying at least one condition selected from the group consisting of a) to c) listed below:

a) polyacrylamide gel polymerized at a high temperature;
b) polyacrylamide gel containing a high concentration of ammonium persulfate; and
c) polyacrylamide gel homogenized by stirring and degassed prior to polymerization.

Since IgM has a very high molecular weight, approximately one million, the polymeric structure (pentamer and hexamer) is difficult to quantitatively analyze using conventional methods. A reported method for analyzing the IgM polymeric structure uses RI-labeled IgM for non-reducing SDS-PAGE (Reference 6/J. Immunol. (1994) 152; 1206). This method requires RI. To develop IgM as a drug, a technique which enables analysis of the IgM polymeric structure in manufacturing processes is necessary. Specifically, analysis of the IgM polymeric structure is required in all the steps of manufacturing, including selection of producing cells, monitoring of cell culture, purification, primary drug manufacturing, and pharmaceutical preparation. RI-free methods are desired for analyzing IgM in these steps. The present inventors discovered that the IgM polymers can be analyzed using the conditions described above, and thereby completed the present invention. Each of the conditions is described in detail below.

a) Polyacrylamide Gel Polymerized at a High Temperature:

Generally, polyacrylamide gel used in electrophoresis of proteins such as immunoglobulin is polymerized at room temperature. In contrast, polyacrylamide gel polymerized at, for example, 37° C. or higher, preferably 40 to 60° C., is useful for the method for analyzing IgM of the present invention. Such a high temperature condition allows acrylamide to be polymerized quickly.

b) Polyacrylamide Gel Containing a High Concentration of Ammonium Persulfate (Aps):

Generally, polyacrylamide gel for SDS-polyacrylamide gel electrophoresis contains approximately 0.05% APS. In contrast, polyacrylamide gel containing, for example, 0.25% or more, preferably 0.1 to 0.5% APS is useful for the method for analyzing IgM of the present invention.

c) Polyacrylamide Gel Homogenized by Stirring and Degassed Prior to Polymerization:

It is important that polyacrylamide gel for electrophoretic analysis is homogeneously prepared without bubbling. Therefore, after addition of a polyacrylamide gel polymerization initiator, polymerization solution is adequately stirred with care to avoid bubbling. In contrast, in the present invention, polymerization solution was more perfectly stirred and homogenized using HYBRID MIXER (KEYENCE) and degassed to prevent bubbling, achieving a homogeneous gel.

The method for analyzing IgM of the present invention can be conducted using the polyacrylamide gel satisfying at least one of the aforementioned conditions a) to c). To analyze IgM at a high accuracy, with its polymeric structures retained, a polyacrylamide gel satisfying preferably at least two or more of the conditions a) to c), more preferably satisfying all the conditions a) to c) may be used.

In analyzing IgM according to the present invention, any buffer can be used as the buffer for electrophoresis. For example, the Tris-acetate SDS electrophoresis buffer is a preferred buffer for the method for analyzing IgM of the present invention. The specific composition of the Tris-acetate SDS electrophoresis buffer is shown in the Examples below.

The method for analyzing IgM of the present invention can analyze the pentamer and/or hexamer IgM. As used herein, "analyzing IgM" means to reveal whether the IgM molecule has a pentamer structure or a hexamer structure. As used herein, the pentamer refers to the IgM having five IgM constituent units, each of which is composed of two molecules of H chain and two molecules of L chain. Similarly, the hexamer refers to the IgM having six constituent units.

The "pentamer structure" or "hexamer structure" of the IgM molecule indicates the pentamer structure or hexamer structure, respectively which can be confirmed by a known method (Reference 6/J. Immunol. (1994) 152; 1206). Furthermore, according to the method for analyzing the IgM of the present invention, the content ratio of the pentamer or hexamer IgM can be determined. For example, the IgM in the gel after electrophoresis can be stained with a visible dye or a fluorescent dye directly or after being transferred onto a membrane. Then, the stain intensity or fluorescent intensity can be measured to quantify the structure of the target IgM structure. Specifically, a method for quantifying the pentamer or hexamer IgM of the present invention may be conducted according to the methods described in Examples 3 and 4. In addition, the content ratio of the IgM pentamer and hexamer structures can be estimated by a known method using ultra centrifugation.

The method for analyzing the IgM polymers of the present invention can be used in analyzing the IgM aggregate. As used herein, the aggregate refers to a molecule in which several IgM molecules are covalently bonded together. Formation of the aggregate causes a change in IgM antibody activity. For example, the IgM aggregate, which is a macromolecule, tends to precipitate. Accordingly, to develop IgM as a drug, it is required that the IgM aggregate be quantitatively evaluated. The method for analyzing the IgM polymers of the present invention enables the quantitative evaluation of not only the content ratio of the IgM pentamer and hexamer but also the content ratio of the IgM aggregate.

More specifically, the presence of pentamer (or hexamer) IgM can be determined by conducting SDS-polyacrylamide gel electrophoresis under the above conditions, to determine if the protein migrates to the position corresponding to the molecular weight of the pentamer (or hexamer) and an anti-IgM antibody binds to the protein. When the protein is a purified IgM, the migration position can be visualized by protein staining. Even if it is an unpurified IgM, an IgM band can be identified by immunoblotting analysis using an anti-µ chain antibody. By quantitatively or semi-quantitatively evaluating the intensity of the identified IgM band, the amount of IgM can be determined. Methods for determining the protein amount based on an electrophoresis profile are known.

The method for analyzing the IgM of the preset invention can clearly distinguish the IgM polymeric structure. Thus, the IgM, after electrophoresis, can be detected without radioisotope (RI). As used herein, the analytical method without RI (non-isotopic analysis) refers to an analytical method involving a step of detecting the IgM, after electrophoresis, by any means other than radioisotope. Means other than radioisotope include, for example, detection using protein staining or an affinity substance binding to the IgM. The affinity substance includes, for example, an anti-IgM antibody, protein L, protein A, protein G, and an IgM Fc receptor. According to the analyzing method of the present invention, these affinity substances may be labeled in advance. To label the affinity substances, enzymes or dyes can be used. The enzymes include peroxidase (POD), β-galactosidase (β-GAL), and alkaline phosphatase (ALP). The dyes include fluorescent dyes, luminescent dyes, and chromogenic dyes. These labels are all non-radioactive substances.

The present invention also relates to electrophoresis gels for separating the IgM polymers by SDS-polyacrylamide gel electrophoresis, comprising a polyacrylamide gel satisfying at least one condition selected from the group consisting of a) to c) below. Furthermore, the present invention relates to the use of a polyacrylamide gel satisfying at least one condition selected from the group consisting of a) to c) below in the method for analyzing the IgM polymers.

a) Polyacrylamide gel polymerized at a high temperature;

b) Polyacrylamide gel containing a high concentration of APS (ammonium persulfate); and c) Polyacrylamide gel homogenized by stirring and degassed prior to polymerization.

These polyacrylamide gels are all useful for the method for analyzing the IgM of the present invention. It is demonstrated by the present invention for the first time that the polyacrylamide gel satisfying at least one of the conditions a) to c) is useful for IgM analysis. The preferred polyacrylamide gels of the present invention satisfy two or more of the conditions a) to c), more preferably all the conditions a) to c). Moreover, the present invention relates to a method for manufacturing an electrophoresis gel for separating the IgM polymers by SDS-polyacrylamide gel electrophoresis, comprising at least one step selected from the group consisting of:

a) polymerizing acrylamide at a high temperature;

b) adding a high concentration of ammonium persulfate to acrylamide; and c) homogenizing acrylamide by stirring and degassed prior to polymerization.

The preferred methods for manufacturing a polyacrylamide gel of the present invention involves two or more of the steps a) to c), more preferably all the steps a) to c). Specifically, the present invention provides a method for manufacturing an electrophoresis gel for separating the IgM polymers by SDS-polyacrylamide gel electrophoresis, which includes the following steps a) to c):

1) adding a high concentration of ammonium persulfate to acrylamide;
2) homogenizing the acrylamide by stirring and degassed prior to polymerization; and
3) polymerizing the acrylamide at a high temperature.

All the cited prior art references are herein incorporated by reference in their entirety.

BEST MODE FOR CARRYING OUT THE INVENTION

Figure 1:
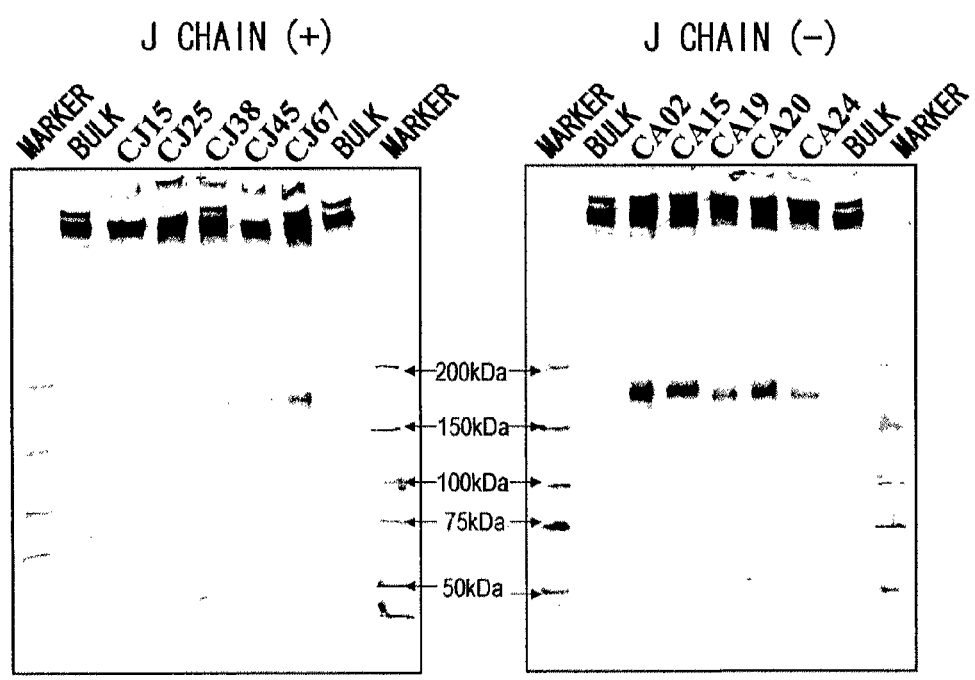
FIG. 1 is a set of photographs showing the results of Western blot of recombinant L612 in culture supernatant. The left-hand panel (J chain +) shows the results of the culture supernatants of the J chain-expressing transformed cells, and the right-hand panel (J chain −) shows the results of the transformed cells into which no J chain gene had been introduced. Each lane corresponds to the sample described below.
Marker: molecular weight marker
Bulk: L612 purified product
CJ15, CJ25, CJ38, CJ45, and CJ67 on the left-hand photograph (J chain +) show the results of the culture supernatants of L612 expressing stable cell lines obtained in Example 1.5.
CA02, CA15, CA19, CA20, and CA24 on the right-hand photograph (J chain −) show the results of the culture supernatants of L612 expressing stable cell lines obtained in Example 1.5.

The present invention is illustrated in more detail below with reference to Examples.

EXAMPLE 1

Preparation of Recombinant L612 Human Antibody to Ganglioside GM3

1.1 Construction of an Anti-Ganglioside GM3 Human Antibody H Chain Gene

A gene encoding an H chain of a human antibody binding to ganglioside GM3 (hereinafter referred to as L612) was amplified by RT-PCR using total RNA extracted from human B cells transformed with Epstein-Barr virus (hereinafter referred to as L612-expressing B cells). A nucleotide sequence of an H chain variable region gene of L612 has been reported by Hoon et al. (Cancer Research 1993; 53:5244-5250).

Total RNA was extracted from $1\times10^7$ L612-expressing B cells using RNeasy Plant Mini Kits (QIAGEN). Based on the nucleotide sequence of the IgM H chain constant region, two oligonucleotides (LMH-f3, LMH-r3) were designed. LMH-f3 (SEQ ID NO: 7) and LMH-r3 (SEQ ID NO: 8) were synthesized in sense and antisense directions, respectively.

The 5'-and 3'-cDNA fragments were separately amplified with 1 μg total RNA by SMART RACE cDNA Amplification Kit (CLONTECH). The 5'-cDNA was amplified with synthetic oligonucleotide LMH-r3 and the 3'-cDNA with synthetic oligonucleotide LMH-f3. Reverse transcription was performed at 42° C. for 1 hour 30 minutes.

The composition of the PCR solution (50 μL) is shown below.
5 μL of 10× Advantage 2 PCR Buffer,
5 μL, of 10× Universal Primer A Mix,
0.2 mM dNTPs (dATP, dGTP, dCTP, dTTP),
1 μL of Advantage 2 Polymerase Mix, (all of the above components are provided from CLONTECH)
2.5 μL of reverse transcription product, and
10 pmole of synthetic oligonucleotide LMH-f3 or LMH-r3.

The reaction temperature conditions are shown below.
Initial temperature of 94° C. for 30 seconds
5 cycles of 94° C./5 sec. and 72° C./3 min.
5 cycles of 94° C./5 sec., 70° C./10 sec., and 72° C./3 min.
25 cycles of 94° C./5 sec., 68° C./10 sec., and 72° C./3 min.
Finally, the reaction product was heated at 72° C. for 7 minutes.

The PCR product was purified from an agarose gel using QIAquick Gel Extraction Kit (QIAGEN) and then cloned into pGEM-T Easy vector (Promega). After the nucleotide sequence was determined, an approximately 1.1 kbp fragment obtained by digesting the vector containing the 5'-cDNA gene with restriction enzymes ApaI (Takara) and SacI (Takara) and an approximately 1.1 kbp fragment obtained by digesting the vector containing the 3'-side gene with restriction enzymes ApaI (Takara) and NotI (Takara) were mixed and cloned into pBluescript KS+ Vector (Toyobo) to give the full-length L612 H chain gene.

The full-length gene fragment was amplified with synthetic oligonucleotides LMH-fxho and LMH-rsal to clone it into an animal cell expression vector. LMH-fxho (SEQ ID NO: 11) is a forward primer designed to hybridize to the 5'-end of the L612 H chain gene and to include an XhoI restriction enzyme recognition sequence and Kozak sequence (Kozak, M. J. Mol. Biol. (1987) 196, 947), while LMH-rsal (SEQ ID NO: 12) is a reverse primer designed to hybridize to the 3'-end of the L612 H chain gene and to include a SalI restriction enzyme recognition sequence.

The composition of the PCR solution (50 µL) is shown below.
  5 µL of 10×PCR Buffer,
  1 mM MgSO$_4$,
  0.2 mM dNTPs (dATP, dGTP, dCTP, dTTP),
  1 unit of DNA polymerase KOD-Plus-,
  (all the constituents listed above are from Toyobo)
  10 ng of pBluescript KS+ Vector containing the full-length L612 H chain gene, and
  10 pmole of synthetic oligonucleotides LMH-fxho and LMH-rsal.

The reaction temperature conditions are shown below.
Initial temperature of 94° C. for 2 minutes
30 cycles of 94° C./15 sec., 60° C./30 sec., and 68° C./2 min.
Finally, the reaction product was heated at 72° C. for five minutes.

The amplified gene fragment was digested with the restriction enzymes XhoI (Takara) and SalI (Takara), purified by QIAquick PCR Purification Kit (QIAGEN), and cloned into the restriction enzyme XhoI site of pUCAG. The vector pUCAG is a vector in which the 2.6 kbp fragment obtained by digesting pCXN (Niwa et al., Gene 1991; 108:193-200) with restriction enzyme BamHI is ligated into the restriction enzyme BamHI site of pUC19 vector (Toyobo). The resulting plasmid was named pUCAG/L612 H. The nucleotide and amino acid sequences of the L612 H chain contained in the plasmid are shown in SEQ ID NOs: 1 and 2, respectively.

1.2 Construction of an Anti-Ganglioside GM3 Human Antibody L Chain Gene

A gene encoding an L612 L chain was amplified using total RNA extracted from the L612-expressing B cells by RT-PCR. A nucleotide sequence of an L612 L chain variable region gene has been reported by Hoon et al. (Cancer Research 1993; 53: 5244-5250).

Total RNA was extracted from the L612-expressing B cells in the same manner as Example 1.1. Based on the nucleotide sequence of the IgM L chain constant region, two oligonucleotides (LML-f1, LML-r1) were designed. LML-f1 (SEQ ID NO: 9) and LML-r1 (SEQ ID NO: 10) were synthesized in the sense and antisense directions, respectively. The 5'-and 3'-side gene fragments were separately amplified with 1 µg total RNA by SMART RACE cDNA Amplification Kit (CLONTECH). The 5'-side gene was amplified with synthetic oligonucleotide LML-r1, and the 3'-side gene with synthetic oligonucleotide LML-f1. Reverse transcription was performed at 42° C. for 1 hour and 30 minutes.

The composition of the PCR solution (50 µL) is shown below.
  5 µL of 10× Advantage 2 PCR Buffer,
  5 µL of 10× Universal Primer A Mix,
  0.2 mM dNTPs (dATP, dGTP, dCTP, dTTP),
  1 µL of Advantage 2 Polymerase Mix,
  (all the constituents listed above are from CLONTECH)
  2.5 µL of reverse transcription product, and
  10 pmole of synthetic oligonucleotide LML-f1 or LML-r1.

The reaction temperature conditions are shown below.
Initial temperature of 94° C. for 30 sec.
5 cycles of 94° C./5 sec. and 72° C./3 min.
5 cycles of 94° C./5 sec., 70° C./10 sec., and 72° C./3 min.
25 cycles of 94° C./5 sec., 68° C./10 sec., 72° C./3 min.
Finally, the reaction product was heated at 72° C. for 7 minutes.

The PCR product was purified from an agarose gel using QIAquick Gel Extraction Kit (QIAGEN) and then cloned into the pGEM-T Easy vector (Promega). After the determination of the nucleotide sequences, an approximately 0.7 kbp fragment obtained by digesting the vector containing the 5'-side gene with restriction enzyme EcoRI (Takara) and an approximately 0.9 kbp fragment obtained by digesting the vector containing the 3'-side gene with restriction enzyme EcoRI (Takara) were mixed, and the full-length gene fragment was amplified with the synthetic oligonucleotides LML-feco and LML-mot. LML-feco (SEQ ID NO: 13) is a forward primer designed to hybridize to the 5'-end of the L612 L chain gene and to include a EcoRI restriction enzyme recognition sequence and Kozak sequence, while LML-mot (SEQ ID NO: 14) is a reverse primer designed to hybridize to the 3'-end of the L612 L chain gene and to include a NotI restriction enzyme recognition sequence.

The composition of the PCR solution (50 µL) is shown below.
  5 µL of 10×PCR Buffer,
  1 mM MgSO$_4$,
  0.2 mM dNTPs (dATP, dGTP, dCTP, dTTP),
  1 unit of DNA polymerase KOD-Plus-,
  (all the constituents listed above are from Toyobo)
  5'-side gene fragment,
  3'-side gene fragment, and
  10 pmole of synthetic oligonucleotides LML-feco and LML-rnot.

The reaction temperature conditions are shown below.
Initial temperature of 94° C. for 2 minutes
30 cycles of 94° C./15 sec., 60° C./30 sec., and 68° C./2 min.
Finally, the reaction product was heated at 72° C. for 5 minutes.

The amplified gene fragment was digested with the restriction enzymes EcoRI (Takara) and NotI (Takara), purified using QIAquick PCR Purification Kit (QIAGEN), and cloned into restriction enzyme EcoRI-NotI site in pCXND3.

The vector pCXND3 was constructed as follows. DHFR-ΔE-rvH-PM1-f (see WO92/19759) was digested at the restriction enzyme EcoRI/SmaI sites to separate the antibody H chain gene from the vector. After only the vector portion was collected, EcoRI-NotI-BamHI adaptor (Takara) was cloned. The resulting vector was named pCHOI.

The DHFR gene expression site of pCHOI was cloned into the restriction enzyme HindIII site of pCXN (Niwa et al., Gene 1991; 108: 193-200), and the resulting vector was named pCXND3. The L chain gene fragment was cloned into pCXND3 and the resulting plasmid was named pCXND3/L612L. The nucleotide and amino acid sequences of the L612 L chain contained in the plasmid are shown in SEQ ID NOs: 3 and 4, respectively.

1.3 Construction of an Anti-Ganglioside GM3 Human Antibody Expression Vector

To prepare an L612 expression vector, an approximately 4.0 kbp fragment obtained by digesting pUCAG/L612 H with the restriction enzyme HindIII (Takara) was cloned into the restriction enzyme HindIII site of pCXND3/L612L. The resulting plasmid was named pCXND3/L612IgM. The plasmid expresses a neomycin-resistant gene, a DHFR gene, and the L612 gene in animal cells.

1.4 Construction of an Anti-Ganglioside GM3 Human Antibody J Chain Gene and Expression Vector A gene encoding an L612 J chain was amplified using total RNA extracted from the L612-expressing B cells by RT-PCR. Total RNA was extracted from the L612-expressing B cells in the same manner as that described above. Based on a nucleotide sequence of a human antibody J chain gene registered in GenBank (GenBank No.: M12759), two oligonucleotides (J-f1, J-r1) were designed and synthesized. J-f1 (SEQ ID NO: 15) is in the sense direction and hybridizes to the human antibody J chain gene Exon3, and J-r1 (SEQ ID NO: 16) is in the antisense direction and hybridizes to the human antibody J chain gene Exon4.

The 5'-and 3'-side gene fragments were separately amplified with 1 μg total RNA using SMART RACE cDNA Amplification Kit (CLONTECH). The 5'-side gene was amplified with the synthetic oligonucleotide J-r1 while the 3'-side gene with the synthetic oligonucleotide J-f1. Reverse transcription was performed at 42° C. for 1 hour 30 minutes.

The composition of the PCR solution (50 μL) is shown below.
5 μL of 10× Advantage 2 PCR Buffer,
5 μL of 10× Universal Primer A Mix,
0.2 mM dNTPs (dATP, dGTP, dCTP, dTTP),
1 μL of Advantage 2 Polymerase Mix,
(all the constituents listed above are from CLONTECH)
2.5 μL of reverse transcription product, and
10 pmole of synthetic oligonucleotide J-f1 or J-r1.
The reaction temperature conditions are shown below.
Initial temperature of 94° C. for 30 sec.
5 cycles of 94° C./5 sec. and 72° C./3 min.
5 cycles of 94° C./5 sec., 70° C./10 sec., and 72° C./3 min.
25 cycles of 94° C./5 sec., 68° C./10 sec., and 72° C./3 min.
Finally, the reaction product was heated at 72° C. for seven minutes.

The PCR product was purified from an agarose gel using QIAquick Gel Extraction Kit (QIAGEN) and cloned in the pGEM-T Easy vector (Promega).

After the determination of the nucleotide sequences, an approximately 0.5 kbp fragment obtained by digesting the vector containing the 5'-side gene with the restriction enzyme EcoRI (Takara) and an approximately 1.0 kbp fragment obtained by digesting the vector containing the 3'-side gene with the restriction enzyme EcoRI (Takara) were mixed and the full-length gene fragment was amplified using the synthetic oligonucleotides J-feco and J-rxba.

J-feco (SEQ ID NO: 17) is a forward primer designed to hybridize to the 5'-end of the L612 J chain gene and to include an EcoRI restriction enzyme recognition sequence and Kozak sequence, while J-rxba (SEQ ID NO: 18) is a reverse primer designed to hybridize to the 3'-end of the L612 J chain gene and to include a XbaI restriction enzyme recognition sequence.

The composition of the PCR solution (50 μL) is shown below.
5 μL 10×PCR Buffer,
1 mM MgSO$_4$,
0.2 mM dNTPs (dATP, dGTP, dCTP, dTTP),
1 unit of DNA polymerase KOD-Plus-,
(all the constituents listed above are from Toyobo)
5'-side gene fragment,
3'-side gene fragment, and
10 pmole of synthetic oligonucleotides J-feco and J-rxba.
The reaction temperature conditions are shown below.
Initial temperature of 94° C. for 2 minutes
30 cycles of 94° C./15 sec., 60° C./30 sec., and 68° C./2 min.
Finally, the reaction product was heated at 72° C. for 5 minutes.

The amplified gene fragment was digested with the restriction enzymes EcoRI (Takara) and XbaI (Takara), purified using QIAquick PCR Purification Kit (QIAGEN), and cloned into restriction enzyme EcoRI-XbaI site of pCOSII-Zeo.

The vector pCOSII-Zeo is a vector obtained by removing the DHFR gene expression site from the above-described pCHOI and cloning the Zeocin-resistant gene expression site. The resulting plasmid was named pCOSII-Zeo/J chain. The nucleotide and amino acid sequences of the L612 J chain contained in the plasmid are shown in SEQ ID NOs: 5 and 6, respectively.

1.5 Expression of the Anti-Ganglioside GM3 Human Antibody Using Animal Cells

An IgM expressing stable cell line was prepared with CHO cells (DG44 cell line) in the manner described below. The gene was introduced by electroporation using Gene PulserII (BioRad).

The method used to introduce the gene into the cell line which expresses no J chain is described below. A mixture of L612 expression vector pCXND3/L612IgM (25 μg) and 0.75 ml CHO cells (1×10$^7$ cells/ml) suspended in PBS was cooled on ice for ten minutes and transferred to a cuvette. Then, pulses were applied at 1.5 kV, 25 μFD.

After 10-minute recovery at room temperature, the electroporated cells were suspended in 40 mL of CHO-S-SFMII medium (Invitrogen) containing a one-fold concentration of HT supplement (Invitrogen). A 50-fold diluted solution was prepared in the same medium and dispensed at 100 μl/well in a 96-well culture plate. The cells were cultured in a CO$_2$ incubator (5% CO$_2$) for 24 hours and further cultured with 0.5 mg/mL of Geneticin (Invitrogen) for two weeks.

The amount of IgM in the culture supernatant of the wells that showed a colony of the transformed cells exhibiting Geneticin-resistance was measured by the concentration quantification method shown in Example 1.6. L612 highly expressing cell lines were subcultured and expanded, and the L612 expressing stable cell lines CA02, CA15, CA19, CA20, and CA24 were obtained.

The method used to introduce the gene into the cell line which expresses the J chain is described below. A mixture of the L612 expression vector pCXND3/L612IgM (25 μg), the J chain expression vector pCOSII-Zeo/J chain (20 μg), and 0.75 ml CHO cells (1×10$^7$ cells/ml) suspended in PBS was cooled on ice for 10 minutes, transferred to a cuvette, and pulses were applied at 1.5 kV, 25 μFD.

After 10-minute recovery at room temperature, the electroporated cells were suspended in 40 ml of CHO-S-SFMII medium (Invitrogen) containing one-fold concentration of HT supplement (Invitrogen).

A 50-fold diluted solution was prepared in the same medium and dispensed at 100 μl/well in a 96-well culture plate. The cells were cultured in a CO$_2$ incubator (5% CO$_2$) for 24 hours and then further cultured with 0.5 mg/mL Geneticin (Invitrogen) and 0.6 mg/mL Zeocin (Invitrogen) for two weeks. The amount of IgM in the culture supernatant of wells that showed a colony of Geneticin-and Zeocin-resistant transformed cells, was measured by the concentration quantification method shown in Example 1.6. L612 highly expressing cell lines were subcultured and expanded, and L612 expressing stable cell lines (CJ15, CJ25, CJ38, CJ45, and CJ67) were obtained.

1.6 Measurement of the IgM Concentration in the Culture Supernatant

The IgM concentration in the culture supernatant was measured in the following manner. Anti-human IgM (BIOSORCE) was diluted with Coating Buffer (0.1 M NaHCO$_3$, 0.02% NaN$_3$) to achieve 1 μg/ml, added to a 96-well ELISA plate at 100 μl/well, and reacted at 4° C. for 24 hours or more for coating.

Then, the plate was washed with Rinse Buffer, and Diluent Buffer was added at 200 μL/well, and reacted at room temperature for one hour or more for blocking. The compositions of Rinse Buffer and Diluent Buffer are shown below.

Rinse Buffer:
PBS(−)
0.05% Tween 20
Diluent Buffer:
50 mM Tris
1 mM MgCl2
0.15 M NaCl
0.05% Tween 20
0.02% NaN3
1% BSA Then, the culture supernatant appropriately diluted with Diluent Buffer was added at 100 µL/well and reacted at room temperature for one hour. The plate was washed with Rinse Buffer, and goat anti-human IgM alkaline phosphatase conjugated (BIOSORCE) was diluted down to 1/4000 with Diluent Buffer, added at 100 µL/well, and reacted at room temperature for one hour. Finally, after washing with Rinse Buffer, an alkaline phosphatase substrate (SIGMA) was added and the absorbance was measured using spectrophotometer Benchmark Plus (BioRad) at a measurement wavelength of 405 nm and a control wavelength of 655 nm. The IgM concentration was calculated by comparing with the L612 purified product (Hoon et al., Cancer Research 1993; 53:5244-5250).

Each L612 expressing stable cell line was cultured in a 75 cm$^2$ culture flask at an initial cell density of 2×10$^5$ cells/mL and the IgM concentration in the culture supernatant was measured in the manner described above. The results are shown in Table 1. The IgM yield was approximately 20 mg/L after 3 days culture and approximately 50 mg/L after 7 days culture, and the production capability, which indicates the capability of a single cell to produce, was 5 to 19 pg/cell/day. IgM has been considered to be difficult to produce in large amounts because it forms a polymer unlike other immunoglobulins and thus the amount expressed by recombinant forms is small. However, our results showed that recombinant IgM-expressing cells with a high yield can be produced using CHO cells.

TABLE 1

| J chain expression | Cell line | Yield after 3 days culture (mg/L) | Yield after 7 days culture (mg/L) | Production capability (pg/cell/day) |
| --- | --- | --- | --- | --- |
| − | CA02 | 24.1 | 36.9 | 14.1 |
|  | CA15 | 11.8 | 39.7 | 4.9 |
|  | CA19 | 27.1 | 62.3 | 13.1 |
|  | CA20 | 20.2 | 35.4 | 10.5 |
|  | CA24 | 25.0 | 41.5 | 10.7 |
| + | CJ15 | 29.4 | N.T. | 19.4 |
|  | CJ25 | 24.4 | N.T. | 18.1 |
|  | CJ38 | 14.9 | N.T. | 12.4 |
|  | CJ45 | 26.4 | N.T. | 18.7 |
|  | CJ67 | 18.0 | N.T. | 12.8 |

N.T.: Not Tested

EXAMPLE 2

Preparation of Recombinant Human Antibody L55 to Ganglioside GM2

2.1 Construction of an Anti-Ganglioside GM2 Human Antibody H Chain Gene

A gene encoding an H chain of a human antibody (hereinafter referred to as L55) which binds to the ganglioside GM2 was amplified by RT-PCR using total RNA extracted from human B cells (hereinafter referred to as L55-expressing B cells) transformed with Epstein-Barr virus. A nucleotide sequence of an L55H chain variable region gene has been reported by Nishinaka et al. (Immunogenetics 1998; 48: 73-75).

Total RNA was extracted from 1×10$^7$ L55-expressing cells using RNeasy Plant Mini Kits (QIAGEN). Based on the nucleotide sequence of the IgM H chain constant region, two oligonucleotides (LMH-f3, LMH-f3) were designed. LMH-f3 (SEQ ID NO: 7) was synthesized in the sense direction and LMH-f3 (SEQ ID NO: 8) in the antisense direction.

With 1 µg of total RNA, 5'-and 3'-side gene fragments were separately amplified using SMART RACE cDNA Amplification Kit (CLONTECH). The 5'-side gene was amplified with the synthetic oligonucleotide LMH-f3 and the 3'-side gene with the synthetic oligonucleotide LMH-f3. Reverse transcription was performed at 42° C. for 1 hour 30 minutes.

The composition of the PCR solution (50 µL) is shown below.
5 µL of 10× Advantage 2 PCR Buffer,
5 µL of 10× Universal Primer A Mix,
0.2 mM dNTPs (dATP, dGTP, dCTP, dTTP),
1 µL of Advantage 2 Polymerase Mix,
(all the constituents listed above are from CLONTECH)
2.5 µL of reverse transcription product, and
10 pmole of synthetic oligonucleotide LMH-f3 or LMH-f3.

The reaction temperature conditions are shown below.
Initial temperature of 94° C. for 30 sec.
5 cycles of 94° C./5 sec. and 72° C./3 min.
5 cycles of 94° C./5 sec., 70° C./10 sec., and 72° C./3 min.
25 cycles of 94° C./5 sec., 68° C./10 sec., and 72° C./3 min.
Finally, the reaction product was heated at 72° C. for 7 minutes.

The PCR product was purified from an agarose gel using QIAquick Gel Extraction Kit (QIAGEN) and then cloned into the pGEM-T Easy vector (Promega). After the determination of the nucleotide sequences, an approximately 1.1 kbp fragment obtained by digesting the vector containing the 5'-side gene with the restriction enzymes ApaI (Takara) and SacII (Takara) and an approximately 1.1 kbp fragment obtained by digesting the vector containing the 3'-side gene with the restriction enzymes ApaI (Takara) and NotI (Takara) were mixed and cloned into the pBluescript KS+ vector (Toyobo) to give the full-length L55H chain gene.

To clone the gene into an animal cell expression vector, the full-length gene fragment was amplified using the synthetic oligonucleotides LMH-fxho and LMH-rsal. LMH-fxho (SEQ ID NO: 11) is a forward primer designed to hybridize to the 5'-end of the L55H chain gene and to include a XhoI restriction enzyme recognition sequence and Kozak sequence while LMH-rsal (SEQ ID NO: 12) is a reverse primer designed to hybridize to the 3'-end of the L55H chain gene and to include a SalI restriction enzyme recognition sequence.

The composition of the PCR solution (50 µL) is shown below.
5 µL of 10×PCR Buffer,
1 mM MgSO$_4$,
0.2 mM dNTPs (dATP, dGTP, dCTP, dTTP),
1 unit of DNA polymerase KOD-Plus-,
(all the constituents listed above are from Toyobo)
10 ng of pBluescript KS+vector containing the full-length L55H chain gene, and
10 pmole of synthetic oligonucleotides LMH-fxho and LMH-rsal.

The reaction temperature conditions are shown below.
Initial temperature of 94° C. for 2 min.
30 cycles of 94° C./15 sec., 55° C./30 sec., and 68° C./3 min.
Finally, the reaction product was heated at 72° C. for 7 minutes.

The amplified gene fragment was digested with the restriction enzymes XhoI (Takara) and SalI (Takara), purified using QIAquick PCR Purification Kit (QIAGEN), and cloned into the restriction enzyme XhoI site of pUCAG. The resulting plasmid was named pUCAG/L55H. The nucleotide and amino acid sequences of the L55H chain contained in the plasmid are shown in SEQ ID NOs: 19 and 20, respectively.

2.2 Construction of an Anti-Ganglioside GM2 Human Antibody L Chain Gene

A gene encoding an L55 L chain was amplified with total RNA extracted from L55-expressing B cells by RT-PCR. A nucleotide sequence of an L55 L chain variable region gene has been reported by Nishinaka et al. (Immunogenetics 1998; 48: 73-75).

Total RNA was extracted from L55-expressing B cells in the same manner as Example 2.1. Based on the nucleotide sequence of the IgM L chain constant region, two oligonucleotides (LML-f1, LML-r1) were designed. LML-f1 (SEQ ID NO: 9) and LML-r1 (SEQ ID NO: 10) were synthesized in the sense and antisense directions, respectively. The 5'-and 3'-side gene fragments were separately amplified with 1 µg of total RNA by SMART RACE cDNA Amplification Kit (CLONTECH). The 5'-side gene was amplified with synthetic oligonucleotide LML-r1 and the 3'-side gene with synthetic oligonucleotide LML-f1. Reverse transcription was performed at 42° C. for 1 hour and 30 minutes.

The composition of the PCR solution (50 µL) is shown below.
5 µL of 10× Advantage 2 PCR Buffer,
5 µL of 10× Universal Primer A Mix,
0.2 mM dNTPs (dATP, dGTP, dCTP, dTTP),
1 µL of Advantage 2 Polymerase Mix,
(all the constituents listed above are from CLONTECH)
2.5 µL of reverse transcription product, and
10 pmole of synthetic oligonucleotide LML-f1 or LML-r1.

The reaction temperature conditions are shown below.
Initial temperature of 94° C. for 30 sec.
5 cycles of 94° C./5 sec. and 72° C./3 min.
5 cycles of 94° C./5 sec., 70° C./10 sec., and 72° C./3 min.
25 cycles of 94° C./5 sec., 68° C./10 sec., and 72° C./3 mM.
Finally, the reaction product was heated at 72° C. for 7 minutes.

The PCR product was purified from an agarose gel using QIAquick Gel Extraction Kit (QIAGEN) and then cloned into the pGEM-T Easy vector (Promega).

After the determination of the nucleotide sequences, PCR was conducted with forward primer L55-f (SEQ ID NO: 23) designed to hybridize to a sequence in the 5'-side untranslated region and reverse primer L55-r (SEQ ID NO: 24) designed to hybridize to a sequence in the 3'-side untranslated region.

The composition of the PCR solution (50 µL) is shown below.
5 µL of 10× Advantage 2 PCR Buffer,
5 µL of 10× Universal Primer A Mix,
0.2 mM dNTPs (dATP, dGTP, dCTP, dTTP),
1 µL of Advantage 2 Polymerase Mix,
(all the constituents listed above are from CLONTECH)
2.5 µL of reverse transcription product, and
10 pmole of synthetic oligonucleotides L55-f and L55-r.

The reaction temperature conditions are shown below.
Initial temperature of 94° C. for 30 sec.
5 cycles of 94° C./5 sec. and 72° C./3 mM.
5 cycles of 94° C./5 sec., 70° C./10 sec., and 72° C./3 min.
25 cycles of 94° C./5 sec., 68° C./10 sec., 72° C./3 min.
Finally, the reaction product was heated at 72° C. for 7 minutes.

The PCR product was purified from an agarose gel using QIAquick Gel Extraction Kit (QIAGEN) and then cloned into the pGEM-T Easy vector (Promega).

After the determination of the nucleotide sequence, the full-length gene fragment was amplified with the synthetic oligonucleotides LML-feco and LML-rnot. LML-feco (SEQ ID NO: 13) is a forward primer designed to hybridize to the 5'-end of the L55 L chain gene and to include an EcoRI restriction enzyme recognition sequence and Kozak sequence while LML-rnot (SEQ ID NO: 14) is a reverse primer designed to hybridize to the 3'-end of the L55 L chain gene and to include a Nod restriction enzyme recognition sequence.

The composition of the PCR solution (50 µL) is shown below.
5 µL of 10×PCR Buffer,
1 mM MgSO$_4$,
0.2 mM dNTPs (dATP, dGTP, dCTP, dTTP),
1 unit of DNA polymerase KOD-Plus-,
(all the constituents listed above are from Toyobo)
10 ng of pGEM-T Easy vector carrying L55 L chain gene, and
10 pmole of synthetic oligonucleotides LML-feco and LML-rnot.

The reaction temperature conditions are shown below.
Initial temperature of 94° C. for 2 minutes
30 cycles of 94° C./15 sec., 55° C./30 sec., and 68° C./3 min.
Finally, the reaction product was heated at 72° C. for 7 minutes.

The amplified gene fragment was digested with the restriction enzymes EcoRI (Takara) and NotI (Takara), purified using QIAquick PCR Purification Kit (QIAGEN), and cloned into the restriction enzyme EcoRI-NotI digested site of pCXND3. The resulting plasmid was named pCXND3/L55L. The nucleotide and amino acid sequences of the L55 L chain contained in the plasmid are shown in SEQ ID NOs: 21 and 22, respectively.

2.3 Construction of an Anti-Ganglioside GM2 Human Antibody Expression Vector

To prepare an L55 expression vector, an approximately 4.0 kbp fragment obtained by digesting pUCAG/L55H with the restriction enzyme HindIII (Takara) was cloned into the restriction enzyme HindIII digested site of pCXND3/L55L. The resulting plasmid was named pCXND3/L55IgM. This plasmid expresses a neomycin-resistant gene, a DHFR gene, and the L55 gene in animal cells.

2.4 Expression of the Anti-Ganglioside GM2 Human Antibody using Animal Cells

Expressing stable cell lines were prepared with CHO cells (DG44 line) as follows. Gene transfer was performed by electroporation using Gene PulserII (BioRad).

The method for transferring the gene to the cell line which does not express the J chain is described below. A mixture of L55 expression vector pCXND3/L55IgM (25 µg) and 0.75 ml of CHO cells (1×10$^7$ cells/ml) suspended in PBS was cooled on ice for 10 minutes and transferred to a cuvette. Then, pulses were applied at 1.5 kV, 25 µFD.

After 10-minute recovery at room temperature, the electroporated cells were suspended in 40 mL of CHO-S-SFMII medium (Invitrogen) containing a one-fold concentration of HT supplement (Invitrogen). A 50-fold diluted solution was prepared in the same medium and dispensed into a 96-well culture plate at 100 μl/well. The cells were cultured in a CO$_2$ incubator (5% CO$_2$) for 24 hours and further cultured with 0.5 mg/mL Geneticin (Invitrogen) for two weeks.

The IgM content in culture supernatants of the wells that showed a colony of transformed cells exhibiting Geneticin-resistance was measured by the concentration quantification method shown in Example 1.6. L55 highly expressing cell lines were subcultured and expanded, and thus the L55 expressing stable cell lines LA24, LA26, LA39, LA66, and LA74 were obtained.

Gene transfer of the cell line which expresses the J chain is described below. A mixture of the L55 expression vector pCXND3/L55IgM (25 μg), the J chain expression vector pCOSII-Zeo/J chain (20 μg) prepared in Example 1.4, and 0.75 ml of CHO cells (1×10$^7$ cells/ml) suspended in PBS was cooled on ice for 10 minutes, transferred into a cuvette, and then pulses were applied at 1.5 kV, 25 μFD.

After 10-minute recovery at room temperature, the electroporated cells were suspended in 40 ml of CHO-S-SFMII medium (Invitrogen) containing one-fold concentration of HT supplement (Invitrogen).

A 50-fold diluted solution was prepared in the same medium and dispensed to a 96-well culture plate at 100 Owen. The cells were cultured in a CO$_2$ incubator (5% CO$_2$) for 24 hours and then further cultured with 0.5 mg/mL Geneticin (Invitrogen) and 0.6 mg/mL Zeocin (Invitrogen) for two weeks. The IgM content in the culture supernatant of the wells that showed a colony of Geneticin-and Zeocin-resistant transformed cells was measured by the concentration quantification method shown in Example 1.6. L55 highly expressing cell lines were subcultured and expanded, and the L55 stably expressing cell lines LJ05, LJ23, LJ32, LJ49, and LJ61 were obtained.

Each L55 stably expressing cell line was cultured in a 75 cm$^2$ culture flask at an initial cell density of 2×10$^5$ cells/mL and the IgM concentration in the culture supernatant was measured in the manner described in Example 1.6. The results are shown in Table 2. The IgM yield was 7 to 70 mg/L after 3 days culture and 50 to 150 mg/L after 7 days culture, and the production capability, which indicates the capability of a single cell to produce, was 5 to 40 pg/cell/day.

The yield was equal to or higher than those of the recombinant L612-producing cell lines shown in Example 1.6. This result demonstrated that recombinant IgM-expressing cell lines having stable high productivity can be prepared from the CHO cells.

TABLE 2

| J chain expression | Cell line | Yield after 3 days culture (mg/L) | Yield after 7 days culture (mg/L) | Production capability (pg/cell/day) |
|---|---|---|---|---|
| − | LA24 | 30.7 | 50.6 | 15.3 |
|   | LA26 | 52.6 | 97.6 | 24.4 |
|   | LA39 | 58.2 | 99.7 | 29.9 |
|   | LA66 | 51.0 | 108.8 | 21.2 |
|   | LA74 | 76.0 | 159.4 | 40.7 |
| + | LJ05 | 44.4 | 82.5 | 21.3 |
|   | LJ23 | 17.1 | N.T. | 8.6 |
|   | LJ32 | 19.8 | 48.6 | 11.2 |
|   | LJ49 | 6.9 | N.T. | 5.2 |
|   | LJ61 | 26.4 | 53.7 | 14.9 |

N.T.: Not Tested

EXAMPLE 3

3.1 Analysis of Polymerization of Recombinant L612 (Example 1) and Recombinant L55 (Example 2)

The recombinant L612 (Example 1) and recombinant L55 polymers were analyzed using non-reducing SDS-PAGE. The electrophoresis gel for non-reducing SDS-PAGE was prepared in the manner described below. 1.80 mL of 30% acrylamide (C %=3.33%), 3.75 mL of 1.50 M Tris-HCl (pH8.8), 3.39 mL of milli Q water, and 2.25 mL of glycerol were admixed in a vessel designed for HYBRID MIXER (TOMY), and the resulting solution was kept at 50° C. Then, 3.75 mL of 2.0% agarose was added and the mixture was kept at 50° C. again.

Then, the mixture was left to stand at room temperature for one minute, 12 μL of TEMED and 50 μL of 25% ammonium persulfate (APS) were added thereto, followed by stirring in HYBRID MIXER (TOMY) for 15 seconds, and degassing for 15 seconds. The solution was collected using a disposable syringe, poured into a gel plate, and acrylamide was allowed to polymerize at 37° C. for one hour. Then, the agarose was solidified at room temperature and the resulting electrophoresis gel was stored at 4° C.

An electrophoresis buffer was prepared by diluting NuPAGE Tris-Acetate 20× running buffer (Invitrogen) down to 1/20 with milli Q water. For 2× sample buffer, 125 mM Tris-HCl (pH6.8), 4.0% SDS, 30% glycerol, and 0.004% Bromophenol blue were used.

The culture supernatants of the recombinant L612 (Example 1, J chain + and J chain −) and the recombinant L55 (Example 2, J chain + and J chain −) obtained in Examples 1 and 2 were subjected to electrophoresis using the above electrophoresis gel, electrophoresis buffer, and 2× sample buffer at a constant voltage of 60 V for 13 hours. Then, Western blot was performed using an anti-μ chain antibody as a primary antibody. Western blot was conducted in the manner described below.

Figure 2:
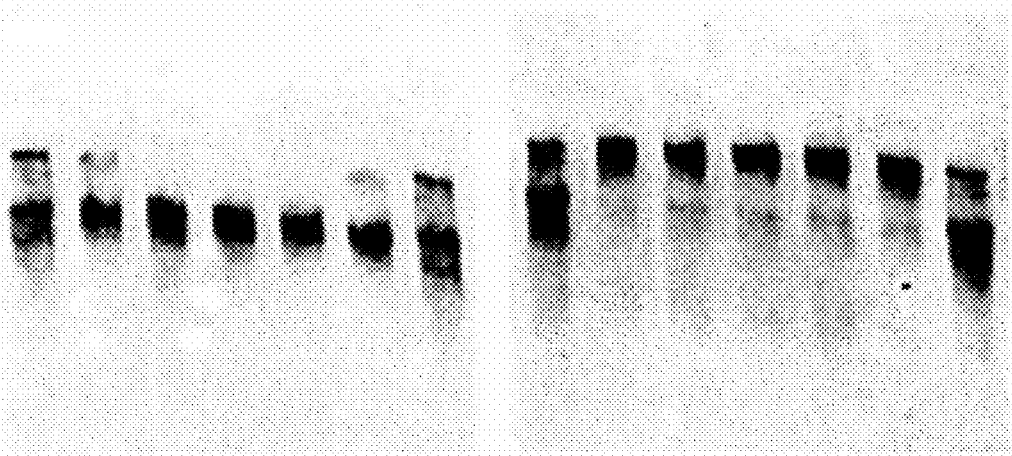
FIG. 2 is a set of photographs showing the results of Western blot of recombinant L55 in culture supernatant. The left-hand panel (J chain +) shows the analysis on the culture supernatants of the transformed cells into which no J chain gene had been introduced, and the right-hand panel (J chain −) shows the analysis on the culture supernatants of the J chain-expressing transformed cells. Each lane corresponds to the sample described below. St: L55 purified product
05, 23, 32, 49, and 61 on the left-hand photograph (J chain +) show the results of the culture supernatants of L55 expressing stable cell lines LJ05, LJ23, LJ32, LJ49, and LJ61 obtained in Example 2.3, respectively.
24, 26, 39, 66, and 74 on the right-hand photograph (J chain −) show the results of the culture supernatants of L55 stably expressing cell lines LA24, LA26, LA39, LA66, and LA74 obtained in Example 2.4, respectively.

After the electrophoresis, the gel was subjected to transfer onto a PVDF membrane using a semi-dry blotting device. After the transfer, blocking was conducted using 5% skim milk containing 0.05% Tween 80 for two hours. The membrane was washed with a Tris-buffered-saline solution containing 0.05% Tween 80 and then reacted for one hour using Rabbit anti-Human IgM (DAKO) diluted to 1/3000 as a primary antibody. After washed again, it was allowed to react for one hour using AP-Goat Rabbit anti-IgG (H+L) Double staining grade (ZYMED) diluted to 1/1000 as a secondary antibody. After being washed again, coloring was performed using Amplified Alkaline Phosphatase Immuno-Blot Assist Kit (Bio-Rad). As a result, with respect to the recombinant L612 (J chain +), a band corresponding to the L612 pentamer from the L612-expressing B cells was mainly obtained (FIG. 1). For the recombinant L612 (J chain −), a band corresponding to the L612 hexamer from the L612-expressing B cells was mainly obtained. It was confirmed that each of the bands obtained by electrophoresis was the pentamer or hexamer with an electron microscope. For the recombinant L55, similar results were obtained (FIG. 2).

These results revealed that it is possible to confirm the pentamer or hexamer in the culture supernatant of IgM-producing cells. It was also revealed that the recombinant IgM expressed with J chain +mainly forms a pentamer and the recombinant IgM expressed with J chain—mainly forms a hexamer. It was shown that recombinant IgM pentamer and hexamer can selectively be prepared by regulating the presence or absence of J chain.

EXAMPLE 4

Figure 3:
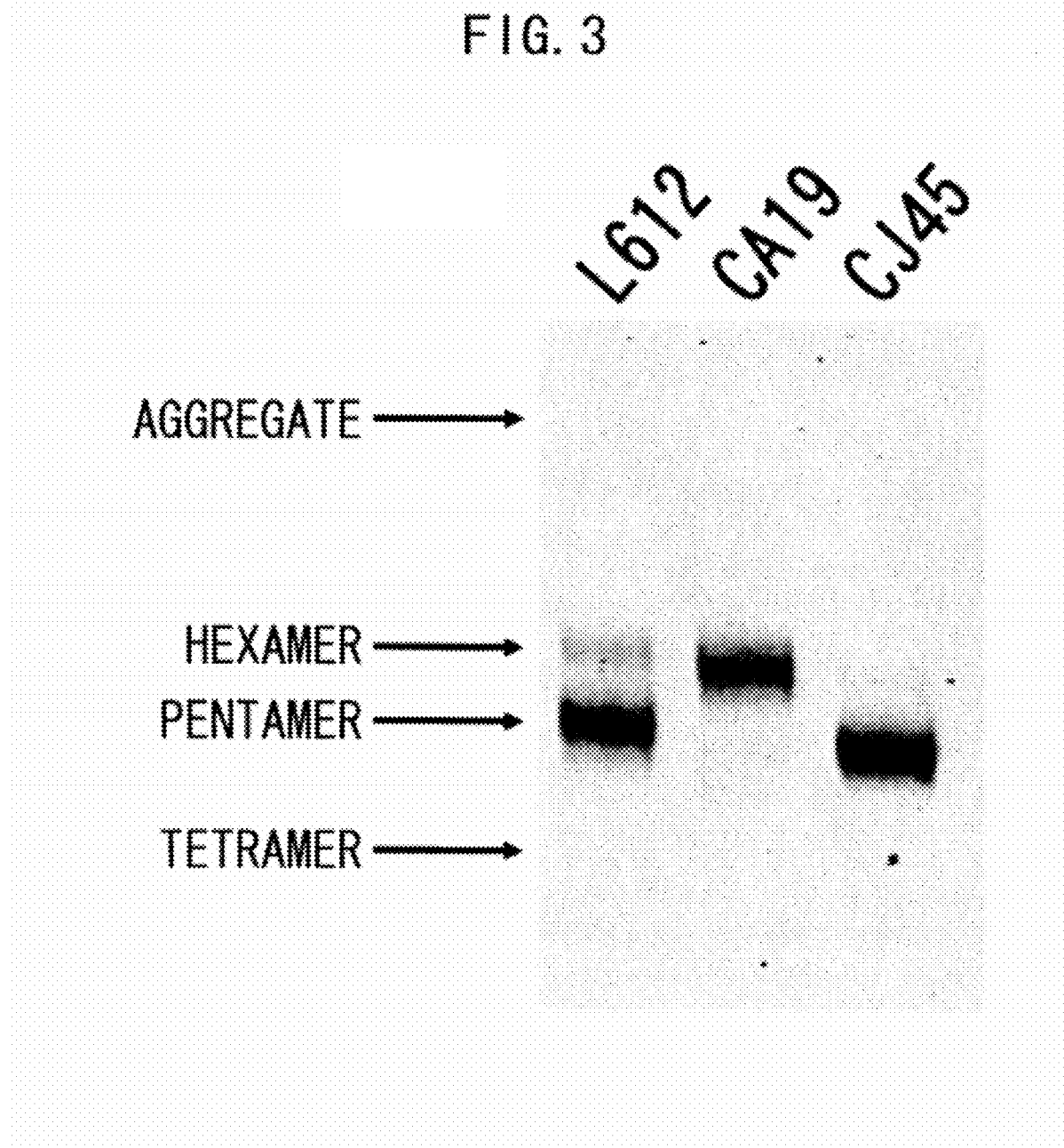
FIG. 3 is a photograph showing the detection of each polymer of the recombinant L612 in culture supernatants. Each lane corresponds to the sample shown below.
L612: L612 purified product
CA19: culture supernatant of L612 expressing stable cell line CA19 obtained in Example 1.5
CJ45: culture supernatant of L612 expressing stable cell line CJ45 obtained in Example 1.5

4.1 Analysis of the Ratio of Polymeric Formation in L612-Expressing Cell Lines Electrophoresis was conducted in a similar manner to Example 3, using non-reducing SDS-PAGE. After electrophoresis, the gel was collected, washed with 10% methanol and 7% acetic acid for 30 minutes or more, and then stained with a Ruby gel stain solution (Bio-Rad) for three hours or more. After staining, the gel was decolorized with 10% methanol and 7% acetic acid for 60 minutes or more. After decolorization, the gel was subjected to detection using FluorImager 595 (Molecular Dynamics) with excitation at 480 nm, and the bands of respective polymers were detected at 618 nm. (FIG. 3). Thus, by preparing densitogram of each lane and obtaining the peak areas, the intensity of each band was quantified. The ratio of the resulting aggregate, hexamer, pentamer, and tetramer is shown in Table 3. It was confirmed that the structures of IgM polymers and aggregates can be quantitatively evaluated according to the method of the present invention.

TABLE 3

|  | J chain | aggregate | hexamer | pentamer | tetramer |
|---|---|---|---|---|---|
| L612 | + | 5% | 18% | 73% | 3% |
| CA19 | − | 5% | 82% | 10% | 3% |
| CJ45 | + | 4% | 6% | 90% | — |

EXAMPLE 5

Establishment of Highly Producing Cell Lines of Recombinant L612 Human Antibody

5.1 Construction of Expression Plasmid pL612CA4

To eliminate the CMV promoter and poly A signal of vector INPEP4 (Patent No. US20010019715), the vector was partially digested with the restriction enzyme PvuII and the approximately 5.5 kb fragment was collected and circularized. This vector was named INPEP4-dCMV. The plasmid expresses a neomycin-resistant gene and a DHFR gene in animal cells.

To introduce a multi-cloning site into INPEP4-dCMV, an adapter sequence (prepared by annealing SEQ ID NOs: 25 and 26) containing the sites for restriction enzymes such as Bg111, XhoI, BamHI, and SalI was cloned into the AscI-FseI site of INPEP4-dCMV. The vector was named INPEP4-dCMV(MCS). The sequences of SEQ ID NOs: 25 and 26 are shown below.

```
                                          (SEQ ID NO: 25)
CCTGATCATGAAGACGTCGACTAGTCCGGATCCCCGGGAGCTCGAGC

GCTCTAGATCTTTAATTAAGG
                                          (SEQ ID NO: 26)
CGCGCCTTAATTAAAGATCTAGAGCGCTCGAGCTCCCGGGGATCCGG

ACTAGTCGACGTCTTCATGATCAGGCCGG
```

To subclone the antibody L chain expression unit, the approximately 3.0 kb fragment obtained by partially digesting pCXND3/L612 μM with SalI and PstI was cloned into the SalI-PstI site of pBluescrip II SK⁺. The vector was named L612CA-L/pBlue.

To introduce the antibody L chain expression unit into the expression vector, the approximately 3.0 kb SalI-BamHI fragment of L612CA-L/pBlue was cloned into the XhoI-BglII site of INPEP4-dCMV(MCS). The vector was named L612CA-L4/dCMV.

To subclone the antibody H chain expression unit, the approximately 4.1 kb SalI-PstI fragment of pCXND3/L612IgM was cloned into the SalI-PstI site of pBluescrip II SK⁺. The vector was named L612CA-H/pBlue.

To introduce the antibody H chain expression unit into the expression vector, the approximately 4.1 kb SalI-BamHI fragment of L612CA-H/pBlue was cloned into the SalI-BamHI site of L612CA-L4/dCMV. The vector was named pL612CA4. The plasmid expresses a neomycin-resistant gene, a DHFR gene, and the L612 gene (H chain, L chain) in animal cells.

5.2 Electroporation, and Geneticin Selection

The genes were transferred into the CHO cell line, DG44, by electroporation. The expression plasmid pL612CA4 was digested with the restriction enzyme PvuI overnight, extracted with phenol and then chloroform, and purified by precipitating with ethanol, and then dissolved in TE. The purified pL612CA4 digested with PvuI was admixed with cells cultured in the CHO-S-SFMII medium (Invitrogen) containing one-fold concentration of HT supplement (Invitrogen), placed into a cuvette, and then transferred with pulses applied using a gene transfer device.

After the gene transfer, the cells in the cuvette were added to 10 mL of CHO-S-SFMII medium (Invitrogen) containing one-fold concentration of HT supplement (Invitrogen), diluted appropriately in the same medium, and then seeded on a 96-well culture plate at 100 μL/well. After plating, the cells were cultured in a $CO_2$ incubator (37° C., 8% $CO_2$). The cells were cultured in the $CO_2$ incubator for one day, and an appropriate amount of Geneticin (Invitrogen) and 100 μL/well of CHO-S-SFMII medium (Invitrogen) containing one-fold concentration of HT supplement (Invitrogen) were added. Then, the cells were further cultured until a colony was formed. The IgM concentration in the culture supernatant of the resulting single colonies was determined according to the method described in Example 1.6. Then, the cells were cultured in an expanded scale on a 24-well culture plate using an appropriate amount of Geneticin (Invitrogen) and CHO-S-SFMII medium (Invitrogen) containing one-fold concentration of HT supplement (Invitrogen). Subsequently, they were subcultured and expanded every three to seven days to select cell lines which produce a large amount of L612.

5.3 MTX Selection

The L612 high production cell lines obtained by Geneticin selection were suspended in the CHO-S-SFMII medium (Invitrogen) containing an appropriate amount of MTX (Methotrexate) and seeded on a 96-well culture plate. After plating, the cells were cultured in a $CO_2$ incubator (37° C., 8% $CO_2$) until a colony was formed. The IgM concentration in the culture supernatant of the resulting single colonies was measured according to the method described in Example 1.6, and then the cells were further cultured in an expanded scale on a 24-well or 48-well culture plate. Subsequently, they were subcultured and expanded every three to seven days to select L612 high production cell lines. By repeating this step while gradually increasing MTX concentration, gene amplification was induced to select the L612 high production cell line shown in Table 4.

TABLE 4

| J chain expression | Cell line | Yield after 3 days culture (mg/L) | Production capability (pg/cell/day) |
|---|---|---|---|
| − | CA4-37-500-3 | 116.7 | 194.6 |

5.4 Method for Measuring the Igm Concentration in the Culture Supernatant (1)

HPLC system: HPLC system Alliance (Waters)
  2487 Dual Absorbance Detector, 2690 Separations Module Millennium 32 ver. 3.21
Column used: GPC column Superose 6 HR 10/30 (Amersham Biosciences)
Standard: Frozen L612 IgM purified product was thawed and centrifuged. The resulting supernatant was aliquoted in a small amount and stored by freezing, which was used as the GPC standard.
Mobile phase: Prepared by adding 0.02% polyoxyethylene (20) Sorbitan monolaurate and 0.05% sodium azide to D-PBS.
HPLC conditions: flow rate of mobile phase, 0.5 mL/min; measurement wavelength, 280 nm; injected sample amount, 100 μL The procedure was as follows. The absorbance of the GPC standard thawed by heating at 37° C. for several minutes was measured at a wavelength of 280 nm using a spectrophotometer, and based on the value, a dilution rate that gives an absorbance of 0.12 at the wavelength of 280 nm was calculated.

The absorbance of an unknown sample was calculated at 280 nm based on the peak area obtained by analyzing the GPC standard diluted at the calculated dilution rate, the peak area and dilution rate of the unknown sample obtained by diluting appropriately and injecting the same volume as that of the standard. The concentration of L612 (μg/mL) was obtained using the measured value for absorbance and the absorbance of L612, $$E^{1\%}_{1\,cm} = 1.4,$$

by the following formula.

L612 concentration(μg/mL)=absorbance(Abs280)
    ÷1.4×1000

5.5 Cloning of Cells in Culture Medium Containing No Mammal-Derived Constituent

The L612 high production cell line obtained by MTX selection was suspended in the culture medium containing an appropriate amount of MTX but no mammal-derived constituent (Invitrogen) and diluted to 1 cell/200 μL by the limiting dilution method. This was seeded on a 96-well culture plate at 100 μL/well. The DG44 cell line cultured in the medium containing one-fold concentration of HT supplement (Invitrogen) but no mammal-derived constituent was suspended in the medium containing an appropriate amount of MTX but no mammal-derived constituent such that the cell amount became $1\times10^5$ cells/mL and then seeded at 100 μL/well. The cells were left to stand in a $CO_2$ incubator (37° C., 8% $CO_2$) Seven days later, 100 μL of culture medium containing appropriate amounts of Geneticin (Invitrogen) and MTX but no mammal-derived constituent was added, and the cells were left to stand in the $CO_2$ incubator (37° C., 8% $CO_2$). Approximately two weeks after, the IgM concentration in the culture supernatant of the resulting single colonies was measured according to the method described in Example 1.6, and the cells were cultured in an expanded scale using the culture medium containing an appropriate amount of MTX but no mammal-derived constituent on a 24-well culture plate. Subsequently, they were subcultured and expanded every three to seven days. Finally, the IgM concentration in the culture supernatant was measured in accordance with the gel filtration chromatography described in 5.4, and the L612 high production clone shown in Table 5 was established.

TABLE 5

| J chain expression | Clone | Yield after 3 days culture (mg/L) | Yield after 7 days culture (mg/L) | Production capability (pg/cell/day) |
|---|---|---|---|---|
| − | PSS-37H3 | 42.0 | 337.2 | 47.0 |

5.6 Method for Measuring the IgM Concentration in the Culture Supernatant (2)

HPLC system: HITACHI LaChrom HPLC device (HITACHI L-7120 pump (A, B), L-7200 autosampler, L-7420 UV-VIS detector, L-7610 degasser)
Data analysis software: model D-7000 Advanced HPLC System Manager (HITACHI)
Column for analysis: TOSHO TSKgel G4000SW$_{XL}$, 7.8 mmID×300 mm (Cat No. 08542, Column No. G0151)
Standard: MABON01R306 (having the same quality as that of the standard in 5.4) was used.
Mobile phase: 50 mM Phosphate-Buffer, 500 mM KCl, pH 7.4, 0.05% $NaN_3$ (pH7.4)
HPLC conditions: 0.5 mL/min (20 min)−>1.0 mL/min, measurement wavelength 280 nm, injected sample amount 100
Calibration curve: calibrated using three points of 1600, 800, and 100 μg/mL 5.7 Batch Culture and Fed Batch Culture of the L612 High Production Cell Line in Culture Medium Containing No Mammal-Derived Constituent The prepared L612 high production cell line was cultured at an initial cell density of $2\times10^5$ cells/mL by the batch or fed batch culture method and the IgM concentration in the culture supernatant was measured by the gel filtration chromatography (see the methods described in 5.4 and 5.6). With the culture medium containing no mammal-derived constituent, yeast extract and fish extract were used as hydrolysates in the batch culture and fed batch culture methods, respectively. As a growth factor, insulin was used for the batch culture, and insulin and insulin-like growth factor-I were used for the fed batch culture. The L612 yield by the batch culture was 269.9 mg/L after 6 days culture (according to the method described in 5.4). On the other hand, the L612 yield by the fed batch culture was 347.4 mg/L after 6 days and 1669.1 mg/L after 14 days culture (according to the method described in 5.6). Since IgM forms polymers unlike other immunoglobulins, its recombinant has less amount of expression. For this reason, it was considered difficult to prepare a large amount of IgM. However, the combined use of hydrolysate and the fed batch culture was shown to enable a high yield of recombinant IgM in the CHO cells.

EXAMPLE 6

Preparation of Pentamer L612 Production Cell Lines Using a Single Expression Vector 6.1 Construction of the Expression Plasmid pL612-pentaCA4

The approximately 4.1 kb SalI-BamHI antibody H chain expression unit was cloned from L612CA-H/pBlue into the XhoI-BglII site of INPEP4-dCMV(MCS) to prepare L612CA-H3/dCMV. The approximately 3.0 kb BamHI-SalI antibody L chain expression unit was cloned from L612CA-L/pBlue into the BamHI-SalI site of L612CA-H3/dCMV to prepare pL612CA3.

To construct an antibody J chain expression unit, the antibody J chain gene was amplified by PCR using pCOSII-Zeo/J chain as template and primers SEQ ID NO: 27: GAGGAAT-TCCACCATGAAGAACC and SEQ ID NO: 28: GAGGCG-GCCGCTTAGTCAGGATAGCAG and cloned into pCR-Blunt II-TOPO (Invitrogen). A SV40 poly A signal was amplified by PCR using pSV2-dhfr (Subramani et al., Mol. Cell. Biol. 1981; 1: 854-864) as template and primers SEQ ID NO: 29: AAAAGCGGCCGCGATCATAATCAGCCAT-ACCA and SEQ ID NO: 30: AAAACTCGAGAAGCTTA-GACATGATAAGATACATTG and cloned into pT7-Blue (Novagen).

The approximately 1.7 kb SpeI-EcoRI fragment of CAG promoter of pCXND3, approximately 0.5 kb EcoRI-NotI fragment of the cloned J chain gene, and approximately 0.3 kb NotI-XhoI fragment of the cloned SV40 poly A signal were combined between the SpeI and XhoI sites of pCR-Blunt II-TOPO. This vector was named pCRCAGproJpA.

By blunting the XhoI site of pCRCAGproJpA and adding a BamHI linker (pCCCGGATCCGGG (SEQ ID NO: 31), TakaraBio) to convert the end to a BamHI site, the antibody J chain expression unit was cloned in the BamHI site of pL612CA3 using the approximately 2.5 kb BamHI fragment. The resulting plasmid was named pL612-pentaCA4.

The plasmid expresses a neomycin-resistant gene, a DHFR gene, and the L612 gene (H chain, L chain, and J chain) in animal cells.

6.2 Electroporation, and Geneticin Selection

Gene transfer to the CHO cell line, DG44, was carried out by electroporation. The expression plasmid pL612-pentaCA4 was digested with the restriction enzyme PvuI overnight, extracted with phenol and then chloroform, purified by precipitating with ethanol, and dissolved in TE. After the cells cultured in the CHO-S-SFMII culture medium (Invitrogen) containing one-fold concentration of HT supplement (Invitrogen) and the purified pL612-pentaCA4 digested with PvuI were mixed and put in a cuvette, pulses were applied using a gene transfer device to carry out gene transfer.

After the gene transfer, the cells in the cuvette were added to 10 mL of the CHO-S-SFMII culture medium (Invitrogen) containing one-fold concentration of HT supplement (Invitrogen), diluted appropriately in the same medium, and seeded on a 96-well culture plate. After plating, the cells were cultured in a $CO_2$ incubator (37° C., 8% $CO_2$) for one day, and an appropriate amount of Geneticin (Invitrogen) and an equivalent amount of CHO-S-SFMII culture medium (Invitrogen) containing one-fold concentration of HT supplement (Invitrogen) were added. The cells were cultured until a colony was formed. The IgM concentration in the culture supernatant of the resulting single colonies was measured according to the method described in Example 1.6 to select the high production cell lines, and the cells were subcultured and expanded every three to seven days to obtain the L612 production cell lines CA4-119 and CA4-139.

6.3 Analysis of Polymer Formation

Figure 4:
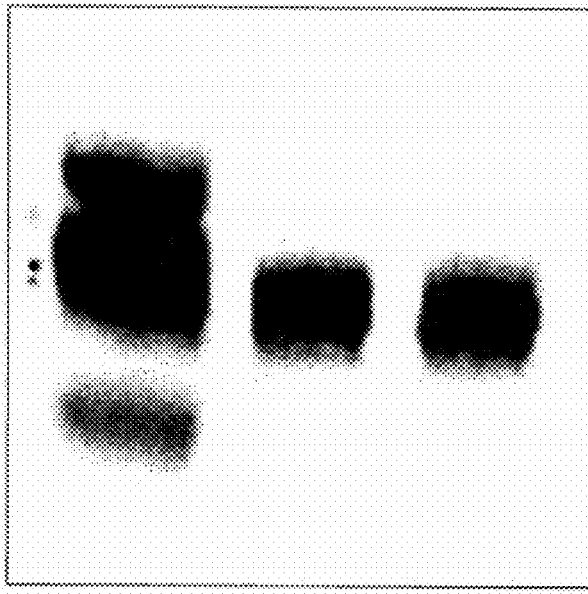
FIG. 4 is a photograph showing the results of analysis of the polymer formation in pL612-pentaCA4-introduced cell lines.

Using the culture supernatant obtained by culturing the cell lines obtained by Geneticin selection for three days with an initial cell density of $2 \times 10^5$ cells/mL in an S100 spinner flask, non-reducing SDS-PAGE was conducted according to the method described in Example 3, and Western blot was performed using anti-human µ chain antibody as the primary antibody. As a result, a band corresponding to the L612 pentamer obtained mainly from L612-expressing B cells was obtained for the pL612-pentaCA4 transformed cell lines, but a band corresponding to the hexamer was not detected (FIG. 4). It was demonstrated that, by placing the J chain expression unit with the H and L chain expression units on a single expression vector and appropriately controlling the expression level of the J chain relative to those of the H and L chains, the pentamer L612 could be mainly produced.

EXAMPLE 7

CDC Activity of the Recombinant L612

Figure 5:
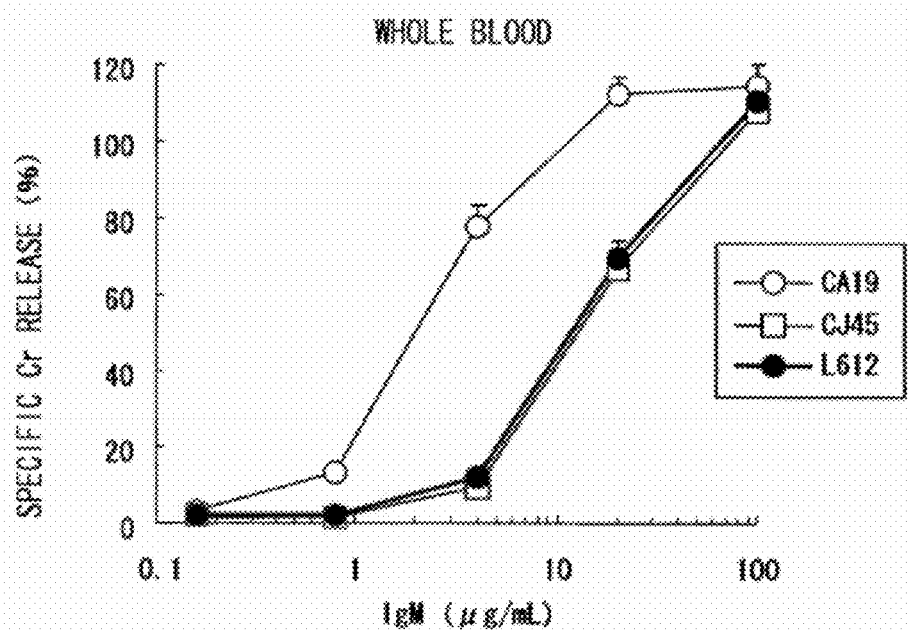
FIG. 5 shows the measured cytotoxic activity of recombinant L612. The upper panel shows the results obtained using addition of whole blood as a complement source, and the lower panel shows the results obtained using addition of undiluted human-derived plasma as a complement source. The vertical axis indicates the percentage (%) of specific $^{51}$Cr release by target cells. The horizontal axis shows the concentration of the antibody (μg/mL).
Figure 5:
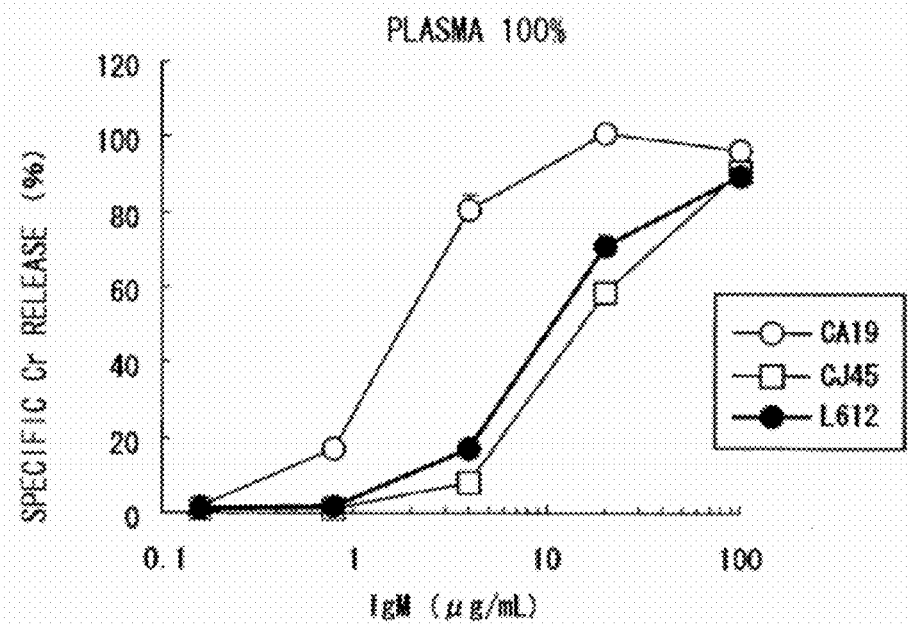

Fifty µL/well of antibody solution diluted appropriately with HAVB was added to M1 melanoma cells ($1 \times 10^4$ cells/50 µL/well), which were target cells radiolabeled with $^{51}$Cr-sodium chromate, so that the final antibody concentrations of the recombinant L612 (J chain –; CA19) or the recombinant L612 (J chain +; CJ45) would be 0.16, 0.8, 4, 20, and 100 µg/mL, and left to stand on ice for 60 minutes. Then, 100 µL of undiluted human-derived plasma or whole blood was added to each well as a complement source and left to stand in a 5% $CO_2$ incubator at 37° C. for 90 minutes. After centrifugation (1000 rpm, 5 min., 4° C.), 100 µL of supernatant was collected from each well to measure the released radioactivity using a γ counter (COBRA II AUTO-GAMMA, MODEL D5005, Packard Instrument Company) (FIG. 5). The CDC activity, or cytotoxic activity (%), was calculated by formula $(A-C)/(B-C) \times 100$. A indicates a radioactivity (cpm) in each well. B indicates an average of radioactivities (cpm) of wells to which 50 µL of target cell suspension, 20 mL of 10% NP-40 aqueous solution (Nonidet® P-40, Code No. 252-23, Nacalai Tesque), and 130 µL of HAVB were added. C indicates an average of radioactivities (cpm) of wells to which 50 µL of target cell suspension and 150 µL of HAVB were added. The experiments were conducted in triplicate, and the average and standard error of percentages of specific chrome release were calculated. Under any condition, the recombinant L612 (CA19) induced a stronger CDC activity than L612, and the ratio of concentrations for 50% lysis induction was 5.8 to 5.9 times. No significant decrease in CDC activity due to coexistence of blood cells was observed.

EXAMPLE 8

Production of the Cell Lines Preferentially Producing the Hexamer IgM (1)

8.1 Construction of the Expression Plasmid p L612CA3

The approximately 4.1 kb SalI-BamHI antibody H chain expression unit was cloned from L612CA-H/pBlue into the XhoI-BglII site of INPEP4-dCMV(MCS) to prepare L612CA-H3/dCMV. The approximately 3.0 kb BamHI-SalI antibody L chain expression unit was cloned from L612CA-L/pBlue into the BamHI-SalI site of L612CA-H3/dCMV to prepare pL612CA3.

8.2 Electroporation, and Geneticin Selection

Gene transfer into the CHO cell line, DG44, was carried out by electroporation. The expression plasmid pL612CA3 was digested with the restriction enzyme PvuI overnight, extracted with phenol and then chloroform, purified by precipitation with ethanol, and dissolved in TE. The cells cultured in the CHO-S-SFMII culture medium (Invitrogen) containing one-fold concentration of HT supplement (Invitrogen) and the purified pL612CA3 digested with PvuI were mixed and put into a cuvette, and then, pulses were applied using a gene transfer device to introduce the gene.

After gene transfer, the cells in the cuvette were added to 10 mL of CHO-S-SFMII culture medium (Invitrogen) containing one-fold concentration of HT supplement (Invitrogen), diluted appropriately in the same medium, and then seeded on a 96-well culture plate. After plating, the cells were cultured in a $CO_2$ incubator (37° C., 8% $CO_2$) for one day, and an appropriate amount of Geneticin (Invitrogen) and the equivalent amount of CHO-S-SFMII culture medium (Invitrogen) containing one-fold concentration of HT supplement (Invitrogen) were added. The cells were further cultured until a colony was formed. The IgM concentration in the culture supernatant of the resulting single colonies was measured according to the method described in Example 1.6 to select high production cell lines, and the cells were subcultured and expanded every three to seven days to give L612 producing cell line CA3-1016.

8.3 MTX Selection

L612 producing cell line CA3-1016 obtained by Geneticin selection was suspended in the CHO-S-SFMII culture medium (Invitrogen) containing an appropriate amount of MTX (Methotrexate) and seeded into a 96-well culture plate. After plating, the cells were cultured in a $CO_2$ incubator (37° C., 8% $CO_2$) until a colony was formed. The IgM concentration in the culture supernatant of the resulting single colonies was measured according to the method described in Example 1.6 to select high production cell lines, and the cells were subcultured and expanded every three to seven days to obtain L612 producing cell line CA3-1016-50-11.

8.4 Batch Culture of the L612 High Production Cell Line in the Culture Medium Containing No Mammal-Derived Constituent The prepared L612 production cell line CA3-1016-50-11 was cultured at an initial cell density of 2 to $3\times10^5$ cells/mL by batch culture and the concentration of the IgM in the culture supernatant was measured according to the gel filtration chromatography method described in Example 5.4. The culture medium was a medium containing no mammal-derived constituent, and yeast extract was used as a hydrolysate. As a growth factor, insulin was used. The yield of L612 by batch culture was 56.0 mg/L after 3 days culture.

8.5 Purification Method

The culture supernatant obtained from batch culture was loaded into an anionic exchange resin column equilibrated with 20 mM sodium phosphate buffer (pH7.4) containing 150 mM NaCl to adsorb the L612, washed with the same equilibration buffer, and then L612 was eluted with 20 mM sodium phosphate buffer (pH7.4) containing 350 mM NaCl. This eluted fraction was loaded into a hydroxyapatite column equilibrated with 10 mM sodium phosphate buffer (pH7.1) to adsorb the L612, washed with the same equilibration buffer, and then the L612 was eluted with 350 mM sodium phosphate buffer (pH7.1). After purifying by separation of impurities by these two kinds of column chromatographies, the aggregate was separated from the resulting L612 fraction by gel filtration using 20 mM acetic acid (pH6.0) containing 300 mM NaCl as the mobile phase. The target fraction collected from gel filtration fractions was filtered through a 0.2 μm membrane filter to obtain the purified L612 fraction.

EXAMPLE 9

Production of Cell Lines Preferentially Producing the Hexamer IgM (2)

9.1 Electroporation, and Geneticin Selection

Gene transfer into the CHO cell line, DG44, was carried out by electroporation. The expression plasmid pCXND3/L612IgM was digested with the restriction enzyme PvuI overnight, extracted with phenol and then chloroform, purified by precipitation with ethanol, and then dissolved in TE. The cells cultured in the CHO-S-SFMII culture medium (Invitrogen) containing one-fold concentration of HT supplement (Invitrogen) and the purified pCXND3/L612IgM digested with PvuI were mixed, put into a cuvette, and pulses were applied using a gene transfer device to introduce the gene.

After gene transfer, the cells in the cuvette were added to 80 mL CHO-S-SFMII medium (Invitrogen, containing no HT), diluted appropriately in the same medium, and then seeded on a 96-well culture plate. After plating, the plate was put in a $CO_2$ incubator (37° C., 8% $CO_2$) to culture until a colony was formed. The IgM concentration in the culture supernatant of the resulting single colonies was measured according to the method described in Example 1.6 to select high production cell lines, and the cells were subcultured and expanded every three to seven days to obtain the L612 production cell line DG44(HT−)-30.

9.2 Continuous Batch Culture of the L612 High Production Cell Line in the Culture Medium Containing No Mammal-Derived Constituent The L612 production cell line DG44(HT−)-30 was cultured at an initial cell density of 2 to $3\times10^5$ cells/mL by continuous batch culture and the IgM concentration in the culture supernatant was measured according to the gel filtration chromatography method described in Example 5.4. The culture medium was CHO-S-SFMII medium (Invitrogen, containing no HT) and yeast extract was used as a hydrolysate. As the growth factor, insulin was used. The L612 yields on every three days for four continuous batch cultures were 28.7 mg/L, 32.0 mg/L, 25.7 mg/L, and 22.2 mg/L, respectively.

9.3 Purification Method

The culture supernatants obtained from the four batch cultures were loaded into anionic exchange resin columns equilibrated with 20 mM sodium phosphate buffer (pH7.4) containing 150 mM NaCl to adsorb the L612, washed with the same equilibration buffer, and the L612 was eluted with 20 mM sodium phosphate buffer (pH 7.4) containing 350 mM NaCl. The resulting eluted fractions were loaded into hydroxyapatite columns equilibrated with 10 mM sodium phosphate buffer (pH 7.1) containing 350 mM NaCl to adsorb the L612, washed with the same equilibration buffer, and then the L612 was eluted with 350 mM sodium phosphate buffer (pH 7.1). After purifying by separation purification of the impurities by these two kinds of column chromatographies, the resulting L612 fractions were separated and the aggregate was removed by gel filtration using 20 mM acetic acid (pH 6.0) containing 300 mM NaCl as the mobile phase. The L612 recovery rates after four purification processes were 83.7%, 45.6%, 63.6%, and 75.6%, as measured by the gel filtration chromatography method described in Example 5.4 The desired fractions obtained by four gel filtrations were combined and filtered through a 0.2 μm membrane filter to obtain the purified L612 fraction.

EXAMPLE 10

Analysis of the Ratio of Polymers in the Cell Line Preferentially Producing the Hexamer IgM The ratio of IgM polymers of the purified L612 fractions obtained in Examples 8 and 9 were analyzed according to the same method as that described in Example 4. The compositions of the electrophoresis gel and electrophoresis buffer were changed as follows.

SDS-PAGE electrophoresis gel was prepared by mixing 1.85 mL of 30% acrylamide (acrylamide: N,N'-methylenebisacrylamide=29:1), 3.75 mL of 1.50 M Tris-Acetate (pH 7.0), 3.34 mL of milli Q water, and 2.25 mL of glycerol in a vessel designed for HYBRID MIXER (TOMY) and keeping the resulting solution at 50° C. 3.75 mL of 2.0% agarose was further added and the mixture was kept at 50° C. again.

The vessel was left to stand at room temperature for one minute, and 12 μL of TEMED and 50 μL of 25% ammonium persulfate (APS) were added, followed by stirring in the HYBRID MIXER (TOMY) for 15 seconds and degassing for 15 seconds. The solution was collected with a disposable syringe and poured into a gel plate, and acrylamide was allowed to polymerize at 37° C. for one hour. Then, the agarose was solidified at room temperature and the resulting electrophoresis gel was stored at 4° C.

A buffer for electrophoresis was prepared using 6.06 g of Tris(hydroxymethyl)aminomethane, 8.96 g of Tricine, and 1 g of SDS with milli Q water to bring up total volume to 1000 mL.

The percentages of aggregate, hexamer, pentamer, and tetramer are shown in Table 6.

TABLE 6

| | J chain | aggregate | hexamer | pentamer | tetramer |
|---|---|---|---|---|---|
| CA3-1016-50-11 | – | 13% | 53% | 27% | 7% |
| DG44(HT-)-30 | – | 11% | 76% | 9% | 4% |

INDUSTRIAL APPLICABILITY

The present invention provides cells having a high IgM-producing ability. The IgM-producing cells generated according to the present invention have a higher IgM-producing ability than the IgM-producing cells established by, for example, the cell fusion method.

Unlike IgG, IgM has a polymeric structure, such as a pentamer or hexamer. For this reason, an increase in yield per cell is generally more difficult to obtain than when using IgG. This means that the IgM-producing cells of the present invention having an increased IgM-producing capability and the methods for producing IgM using these cells are achieved by solving extremely difficult problems.

The present invention also provides a method for respectively producing pentamer IgM and hexamer IgM. It has been already known that the IgM molecule has pentamer and hexamer structures. However, no method for preferentially producing IgM having one structure or the other has been known. The present invention succeeded in preferentially producing the IgM of either pentamer or hexamer structure based on the presence or absence of a J chain in the IgM gene used for transformation.

The hexamer IgM thus produced was shown to have a stronger cytotoxicity than the produced pentamer IgM. The present invention is the first finding of the strong cytotoxicity of a recombinant human IgM in the presence of a human complement using the hexamer-structured recombinant human IgM. Thus, the methods of the present invention are ideal for preferentially producing the hexamer-structured IgM and obtaining an antibody drug with cytotoxic activity of the IgM.

Furthermore, the present invention provides a method for analyzing the pentamer and hexamer IgMs. With known methods, it is difficult to identify the structure of an IgM polymer. According to the analysis method of the present invention, the structure of the IgM polymers can be identified correctly. Using the method for analyzing the IgM of the present invention, the percentage of the pentamer or hexamer in the IgM fractions obtained by a certain production method can be determined correctly. It is important in evaluating IgM producing technology to elucidate the structure of the IgM and its content. In addition, the analysis method of the present invention requires no RI. The analysis method free from RI is useful in evaluating all the steps of the drug manufacturing process.

---

The invention claimed is:

1. A pharmaceutical composition comprising a substantially purified anti-ganglioside GM3 IgM antibody, wherein said IgM antibody
   (a) has a heavy (H) chain comprising SEQ ID NO: 2 and a light (L) chain comprising SEQ ID NO: 4, and
   (b) is recombinantly produced in a non-lymphoid cell.

2. The pharmaceutical composition of claim 1 comprising 80% or more pentamer IgM.

3. The pharmaceutical composition of claim 1 comprising 50% or more hexamer IgM.

4. The pharmaceutical composition of claim 3, comprising 80% or more hexamer IgM.

5. The pharmaceutical composition of claim 1 comprising IgM having a hexamer/pentamer ratio of at least 1.5.

6. The pharmaceutical composition of claim 1, wherein the non-lymphoid cell is a CHO cell.

7. The pharmaceutical composition of claim 1, wherein the IgM is produced by a method comprising
   (a) culturing transformed non-lymphoid cells so that they produce the IgM at a level of at least 100 mg/L or at a level of at least 35 pg/cell/day, and
   (b) collecting the IgM from the culture or a supernatant of the culture.

8. The pharmaceutical composition of claim 1, wherein the substantially pure IgM is obtained by purifying the IgM from a culture supernatant obtained from culturing transformed non-lymphoid cells producing the IgM at a level of at least 100 mg/L or at a level of at least 35 pg/cell/day.

9. The pharmaceutical composition of claim 1, wherein the IgM antibody is produced in the absence of IgM J chain.

10. The pharmaceutical composition of claim 1, wherein the IgM antibody is produced in the presence of IgM J chain.

11. A pharmaceutical composition comprising a substantially purified anti-ganglioside GM2 IgM antibody, wherein said IgM antibody
    (a) has a heavy (H) chain comprising SEQ ID NO: 20 and a light (L) chain comprising SEQ ID NO: 22, and
    (b) is recombinantly produced in a non-lymphoid cell.

12. The pharmaceutical composition of claim 11 comprising 80% or more pentamer IgM.

13. The pharmaceutical composition of claim 11 comprising 50% or more hexamer IgM.

14. The pharmaceutical composition of claim 13, comprising 80% or more hexamer IgM.

15. The pharmaceutical composition of claim 11 comprising IgM having a hexamer/pentamer ratio of at least 1.5.

16. The pharmaceutical composition of claim 11, wherein the non-lymphoid cell is a CHO cell.

17. The pharmaceutical composition of claim 11, wherein the IgM is produced by a method comprising
    (a) culturing transformed non-lymphoid cells so that they produce the IgM at a level of at least 100 mg/L or at a level of at least 35 pg/cell/day, and
    (b) collecting the IgM from the culture or a supernatant of the culture.

18. The pharmaceutical composition of claim 11, wherein the substantially pure IgM is obtained by purifying the IgM from a culture supernatant obtained from culturing transformed non-lymphoid cells producing the IgM at a level of at least 100 mg/L or at a level of at least 35 pg/cell/day.

19. The pharmaceutical composition of claim 11, wherein the IgM antibody is produced in the absence of IgM J chain.

20. The pharmaceutical composition of claim 11, wherein the IgM antibody is produced in the presence of IgM J chain.

* * * * *

SEQUENCE LISTING

```
<160> NUMBER OF SEQ ID NOS: 31

<210> SEQ ID NO 1
<211> LENGTH: 1779
<212> TYPE: DNA
<213> ORGANISM: Homo sapiens
<220> FEATURE:
<221> NAME/KEY: CDS
<222> LOCATION: (1)..(1779)
<223> OTHER INFORMATION:

<400> SEQUENCE: 1 atg gag ttt ggg ctg agc tgg ctt ttt ctt gtg gct att tta aaa ggt      48
Met Glu Phe Gly Leu Ser Trp Leu Phe Leu Val Ala Ile Leu Lys Gly
1               5                   10                  15 gtc cag tgt gag gtg cag ctg ttg gat tct ggg gga ggc ttg gta cag      96
Val Gln Cys Glu Val Gln Leu Leu Asp Ser Gly Gly Gly Leu Val Gln
            20                  25                  30
```

-continued

| | | |
|---|---|---|
| cct ggg ggg tgc ctg aga ctc tcc tgt gca gcc tct gga ttc acc ttt<br>Pro Gly Gly Cys Leu Arg Leu Ser Cys Ala Ala Ser Gly Phe Thr Phe<br>35                            40                            45 | 144 |
| agc agc tgt gcc atg agc tgg gtc cgc cag gct cca ggg aag ggg ctg<br>Ser Ser Cys Ala Met Ser Trp Val Arg Gln Ala Pro Gly Lys Gly Leu<br>    50                         55                        60 | 192 |
| gag tgg gtc tca gct att agt ggt agt ggt ggt agc aca tac tac gca<br>Glu Trp Val Ser Ala Ile Ser Gly Ser Gly Gly Ser Thr Tyr Tyr Ala<br>65                           70                          75                      80 | 240 |
| gac tcc gtg aag ggc cgg ttc acc atc tcc aga gac aaa tcc aag aac<br>Asp Ser Val Lys Gly Arg Phe Thr Ile Ser Arg Asp Lys Ser Lys Asn<br>                85                         90                        95 | 288 |
| acg ttg tat ctg caa atg aac agc ctg aga gcc gag gac acg gcc gta<br>Thr Leu Tyr Leu Gln Met Asn Ser Leu Arg Ala Glu Asp Thr Ala Val<br>                     100                        105                    110 | 336 |
| tat tac tgt gcg aaa ggt ggc aac gat att ttg act ggt tat tat gct<br>Tyr Tyr Cys Ala Lys Gly Gly Asn Asp Ile Leu Thr Gly Tyr Tyr Ala<br>           115                        120                    125 | 384 |
| tgg ggc cag gga acc ctg gtc acc gtc tcc tca ggg agt gca tcc gcc<br>Trp Gly Gln Gly Thr Leu Val Thr Val Ser Ser Gly Ser Ala Ser Ala<br>130                            135                        140 | 432 |
| cca acc ctt ttc ccc ctc gtc tcc tgt gag aat tcc ccg tcg gat acg<br>Pro Thr Leu Phe Pro Leu Val Ser Cys Glu Asn Ser Pro Ser Asp Thr<br>145                          150                        155                    160 | 480 |
| agc agc gtg gcc gtt ggc tgc ctc gca cag gac ttc ctt ccc gac tcc<br>Ser Ser Val Ala Val Gly Cys Leu Ala Gln Asp Phe Leu Pro Asp Ser<br>                   165                        170                    175 | 528 |
| atc act ttc tcc tgg aaa tac aag aac aac tct gac atc agc agc acc<br>Ile Thr Phe Ser Trp Lys Tyr Lys Asn Asn Ser Asp Ile Ser Ser Thr<br>                     180                        185                    190 | 576 |
| cgg ggc ttc cca tca gtc ctg aga ggg ggc aag tac gca gcc acc tca<br>Arg Gly Phe Pro Ser Val Leu Arg Gly Gly Lys Tyr Ala Ala Thr Ser<br>           195                        200                    205 | 624 |
| cag gtg ctg ctg cct tcc aag gac gtc atg cag ggc aca gac gaa cac<br>Gln Val Leu Leu Pro Ser Lys Asp Val Met Gln Gly Thr Asp Glu His<br>210                            215                        220 | 672 |
| gtg gtg tgc aaa gtc cag cac ccc aac ggc aac aaa gaa aag aac gtg<br>Val Val Cys Lys Val Gln His Pro Asn Gly Asn Lys Glu Lys Asn Val<br>225                            230                        235                    240 | 720 |
| cct ctt cca gtg att gct gag ctg cct ccc aaa gtg agc gtc ttc gtc<br>Pro Leu Pro Val Ile Ala Glu Leu Pro Pro Lys Val Ser Val Phe Val<br>                         245                        250                    255 | 768 |
| cca ccc cgc gac ggc ttc ttc ggc aac ccc cgc aag tcc aag ctc atc<br>Pro Pro Arg Asp Gly Phe Phe Gly Asn Pro Arg Lys Ser Lys Leu Ile<br>           260                        265                    270 | 816 |
| tgc cag gcc acg ggt ttc agt ccc cgg cag att cag gtg tcc tgg ctg<br>Cys Gln Ala Thr Gly Phe Ser Pro Arg Gln Ile Gln Val Ser Trp Leu<br>275                            280                        285 | 864 |
| cgc gag ggg aag cag gtg ggg tct ggc gtc acc acg gac cag gtg cag<br>Arg Glu Gly Lys Gln Val Gly Ser Gly Val Thr Thr Asp Gln Val Gln<br>290                            295                        300 | 912 |
| gct gag gcc aaa gag tct ggg ccc acg acc tac aag gtg acc agc aca<br>Ala Glu Ala Lys Glu Ser Gly Pro Thr Thr Tyr Lys Val Thr Ser Thr<br>305                            310                        315                    320 | 960 |
| ctg acc atc aaa gag agc gac tgg ctc ggc cag agc atg ttc acc tgc<br>Leu Thr Ile Lys Glu Ser Asp Trp Leu Gly Gln Ser Met Phe Thr Cys<br>                     325                        330                    335 | 1008 |
| cgc gtg gat cac agg ggc ctg acc ttc cag cag aat gcg tcc tcc atg<br>Arg Val Asp His Arg Gly Leu Thr Phe Gln Gln Asn Ala Ser Ser Met<br>           340                        345                    350 | 1056 |

```
tgt gtc ccc gat caa gac aca gcc atc cgg gtc ttc gcc atc ccc cca    1104
Cys Val Pro Asp Gln Asp Thr Ala Ile Arg Val Phe Ala Ile Pro Pro
        355                 360                 365 tcc ttt gcc agc atc ttc ctc acc aag tcc acc aag ttg acc tgc ctg    1152
Ser Phe Ala Ser Ile Phe Leu Thr Lys Ser Thr Lys Leu Thr Cys Leu
    370                 375                 380 gtc aca gac ctg acc acc tat gac agc gtg acc atc tcc tgg acc cgc    1200
Val Thr Asp Leu Thr Thr Tyr Asp Ser Val Thr Ile Ser Trp Thr Arg
385                 390                 395                 400 cag aat ggc gaa gct gtg aaa acc cac acc aac atc tcc gag agc cac    1248
Gln Asn Gly Glu Ala Val Lys Thr His Thr Asn Ile Ser Glu Ser His
                405                 410                 415 ccc aat gcc act ttc agc gcc gtg ggt gag gcc agc atc tgc gag gat    1296
Pro Asn Ala Thr Phe Ser Ala Val Gly Glu Ala Ser Ile Cys Glu Asp
            420                 425                 430 gac tgg aat tcc ggg gag agg ttc acg tgc acc gtg acc cac aca gac    1344
Asp Trp Asn Ser Gly Glu Arg Phe Thr Cys Thr Val Thr His Thr Asp
        435                 440                 445 ctg ccc tcg cca ctg aag cag acc atc tcc cgg ccc aag ggg gtg gcc    1392
Leu Pro Ser Pro Leu Lys Gln Thr Ile Ser Arg Pro Lys Gly Val Ala
    450                 455                 460 ctg cac agg ccc gat gtc tac ttg ctg cca cca gcc cgg gag cag ctg    1440
Leu His Arg Pro Asp Val Tyr Leu Leu Pro Pro Ala Arg Glu Gln Leu
465                 470                 475                 480 aac ctg cgg gag tcg gcc acc atc acg tgc ctg gtg acg ggc ttc tct    1488
Asn Leu Arg Glu Ser Ala Thr Ile Thr Cys Leu Val Thr Gly Phe Ser
                485                 490                 495 ccc gcg gac gtc ttc gtg cag tgg atg cag agg ggg cag ccc ttg tcc    1536
Pro Ala Asp Val Phe Val Gln Trp Met Gln Arg Gly Gln Pro Leu Ser
            500                 505                 510 ccg gag aag tat gtg acc agc gcc cca atg cct gag ccc cag gcc cca    1584
Pro Glu Lys Tyr Val Thr Ser Ala Pro Met Pro Glu Pro Gln Ala Pro
        515                 520                 525 ggc cgg tac ttc gcc cac agc atc ctg acc gtg tcc gaa gag gaa tgg    1632
Gly Arg Tyr Phe Ala His Ser Ile Leu Thr Val Ser Glu Glu Glu Trp
    530                 535                 540 aac acg ggg gag acc tac acc tgc gtg gtg gcc cat gag gcc ctg ccc    1680
Asn Thr Gly Glu Thr Tyr Thr Cys Val Val Ala His Glu Ala Leu Pro
545                 550                 555                 560 aac agg gtc acc gag agg acc gtg gac aag tcc acc ggt aaa ccc acc    1728
Asn Arg Val Thr Glu Arg Thr Val Asp Lys Ser Thr Gly Lys Pro Thr
                565                 570                 575 ctg tac aac gtg tcc ctg gtc atg tcc gac aca gct ggc acc tgc tac    1776
Leu Tyr Asn Val Ser Leu Val Met Ser Asp Thr Ala Gly Thr Cys Tyr
            580                 585                 590 tga                                                                1779

<210> SEQ ID NO 2
<211> LENGTH: 592
<212> TYPE: PRT
<213> ORGANISM: Homo sapiens

<400> SEQUENCE: 2

Met Glu Phe Gly Leu Ser Trp Leu Phe Leu Val Ala Ile Leu Lys Gly
1               5                   10                  15

Val Gln Cys Glu Val Gln Leu Leu Asp Ser Gly Gly Gly Leu Val Gln
            20                  25                  30

Pro Gly Gly Cys Leu Arg Leu Ser Cys Ala Ala Ser Gly Phe Thr Phe
        35                  40                  45
```

```
Ser Ser Cys Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                      70                  75                  80

Asp Ser Val Lys Gly Arg Phe Thr Ile Ser Arg Asp Lys Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Gly Gly Asn Asp Ile Leu Thr Gly Tyr Tyr Ala
        115                 120                 125

Trp Gly Gln Gly Thr Leu Val Thr Val Ser Ser Gly Ser Ala Ser Ala
    130                 135                 140

Pro Thr Leu Phe Pro Leu Val Ser Cys Glu Asn Ser Pro Ser Asp Thr
145                 150                 155                 160

Ser Ser Val Ala Val Gly Cys Leu Ala Gln Asp Phe Leu Pro Asp Ser
                165                 170                 175

Ile Thr Phe Ser Trp Lys Tyr Lys Asn Asn Ser Asp Ile Ser Ser Thr
            180                 185                 190

Arg Gly Phe Pro Ser Val Leu Arg Gly Gly Lys Tyr Ala Ala Thr Ser
        195                 200                 205

Gln Val Leu Leu Pro Ser Lys Asp Val Met Gln Gly Thr Asp Glu His
    210                 215                 220

Val Val Cys Lys Val Gln His Pro Asn Gly Asn Lys Glu Lys Asn Val
225                 230                 235                 240

Pro Leu Pro Val Ile Ala Glu Leu Pro Pro Lys Val Ser Val Phe Val
                245                 250                 255

Pro Pro Arg Asp Gly Phe Phe Gly Asn Pro Arg Lys Ser Lys Leu Ile
            260                 265                 270

Cys Gln Ala Thr Gly Phe Ser Pro Arg Gln Ile Gln Val Ser Trp Leu
        275                 280                 285

Arg Glu Gly Lys Gln Val Gly Ser Gly Val Thr Thr Asp Gln Val Gln
    290                 295                 300

Ala Glu Ala Lys Glu Ser Gly Pro Thr Thr Tyr Lys Val Thr Ser Thr
305                 310                 315                 320

Leu Thr Ile Lys Glu Ser Asp Trp Leu Gly Gln Ser Met Phe Thr Cys
                325                 330                 335

Arg Val Asp His Arg Gly Leu Thr Phe Gln Gln Asn Ala Ser Ser Met
            340                 345                 350

Cys Val Pro Asp Gln Asp Thr Ala Ile Arg Val Phe Ala Ile Pro Pro
        355                 360                 365

Ser Phe Ala Ser Ile Phe Leu Thr Lys Ser Thr Lys Leu Thr Cys Leu
    370                 375                 380

Val Thr Asp Leu Thr Thr Tyr Asp Ser Val Thr Ile Ser Trp Thr Arg
385                 390                 395                 400

Gln Asn Gly Glu Ala Val Lys Thr His Thr Asn Ile Ser Glu Ser His
                405                 410                 415

Pro Asn Ala Thr Phe Ser Ala Val Gly Glu Ala Ser Ile Cys Glu Asp
            420                 425                 430

Asp Trp Asn Ser Gly Glu Arg Phe Thr Cys Thr Val Thr His Thr Asp
        435                 440                 445

Leu Pro Ser Pro Leu Lys Gln Thr Ile Ser Arg Pro Lys Gly Val Ala
    450                 455                 460

Leu His Arg Pro Asp Val Tyr Leu Leu Pro Pro Ala Arg Glu Gln Leu
465                 470                 475                 480
```

```
Asn Leu Arg Glu Ser Ala Thr Ile Thr Cys Leu Val Thr Gly Phe Ser
            485                 490                 495

Pro Ala Asp Val Phe Gln Trp Met Gln Arg Gly Gln Pro Leu Ser
        500                 505                 510

Pro Glu Lys Tyr Val Thr Ser Ala Pro Met Pro Glu Pro Gln Ala Pro
            515                 520                 525

Gly Arg Tyr Phe Ala His Ser Ile Leu Thr Val Ser Glu Glu Trp
    530                 535                 540

Asn Thr Gly Glu Thr Tyr Thr Cys Val Val Ala His Glu Ala Leu Pro
545                 550                 555                 560

Asn Arg Val Thr Glu Arg Thr Val Asp Lys Ser Thr Gly Lys Pro Thr
                565                 570                 575

Leu Tyr Asn Val Ser Leu Val Met Ser Asp Thr Ala Gly Thr Cys Tyr
            580                 585                 590

<210> SEQ ID NO 3
<211> LENGTH: 723
<212> TYPE: DNA
<213> ORGANISM: Homo sapiens
<220> FEATURE:
<221> NAME/KEY: CDS
<222> LOCATION: (1)..(723)
<223> OTHER INFORMATION:

<400> SEQUENCE: 3
```

| | | |
|---|---|---|
| atg gtg ttg cag acc cag gtc ttc att tct ctg ttg ctc tgg atc tct<br>Met Val Leu Gln Thr Gln Val Phe Ile Ser Leu Leu Leu Trp Ile Ser<br>1               5                   10                  15 | 48 |
| ggt gcc tac ggg gac atc gtg atg acc cag tct cca gac tcc ctg gct<br>Gly Ala Tyr Gly Asp Ile Val Met Thr Gln Ser Pro Asp Ser Leu Ala<br>            20                  25                  30 | 96 |
| gtg tct ctg ggc gag agg gcc acc atc aac tgc aag tcc agc cag agt<br>Val Ser Leu Gly Glu Arg Ala Thr Ile Asn Cys Lys Ser Ser Gln Ser<br>        35                  40                  45 | 144 |
| gtt tta tac agc tcc aac aat aag aac tac tta gct tgg tac cag cag<br>Val Leu Tyr Ser Ser Asn Asn Lys Asn Tyr Leu Ala Trp Tyr Gln Gln<br>    50                  55                  60 | 192 |
| aaa cca gga cag cct cct aag ctg ctc att tac tgg gca tct acc cgg<br>Lys Pro Gly Gln Pro Pro Lys Leu Leu Ile Tyr Trp Ala Ser Thr Arg<br>65                  70                  75                  80 | 240 |
| gaa tcc ggg gtc cct gac cga ttc agt ggc agc ggg tct ggg aca gat<br>Glu Ser Gly Val Pro Asp Arg Phe Ser Gly Ser Gly Ser Gly Thr Asp<br>                85                  90                  95 | 288 |
| ttc act ctc acc atc agc agc ctg cag gct gaa gat gtg gca gtt tat<br>Phe Thr Leu Thr Ile Ser Ser Leu Gln Ala Glu Asp Val Ala Val Tyr<br>            100                 105                 110 | 336 |
| tac tgt cag caa tat tat agt act cct ccg acg ttc ggc caa ggg acc<br>Tyr Cys Gln Gln Tyr Tyr Ser Thr Pro Pro Thr Phe Gly Gln Gly Thr<br>        115                 120                 125 | 384 |
| aag gtg gaa atc aaa cga act gtg gct gca cca tct gtc ttc atc ttc<br>Lys Val Glu Ile Lys Arg Thr Val Ala Ala Pro Ser Val Phe Ile Phe<br>    130                 135                 140 | 432 |
| ccg cca tct gat gag cag ttg aaa tct gga act gcc tct gtt gtg tgc<br>Pro Pro Ser Asp Glu Gln Leu Lys Ser Gly Thr Ala Ser Val Val Cys<br>145                 150                 155                 160 | 480 |
| ctg ctg aat aac ttc tat ccc aga gag gcc aaa gta cag tgg aag gtg<br>Leu Leu Asn Asn Phe Tyr Pro Arg Glu Ala Lys Val Gln Trp Lys Val<br>                165                 170                 175 | 528 |
| gat aac gcc ctc caa tcg ggt aac tcc cag gag agt gtc aca gag cag<br>Asp Asn Ala Leu Gln Ser Gly Asn Ser Gln Glu Ser Val Thr Glu Gln | 576 |

```
                      180                 185                 190
gac agc aag gac agc acc tac agc ctc agc agc acc ctg acg ctg agc      624
Asp Ser Lys Asp Ser Thr Tyr Ser Leu Ser Ser Thr Leu Thr Leu Ser
        195                 200                 205 aaa gca gac tac gag aaa cac aaa gtc tac gcc tgc gaa gtc acc cat      672
Lys Ala Asp Tyr Glu Lys His Lys Val Tyr Ala Cys Glu Val Thr His
210                 215                 220 cag ggc ctg agc tcg ccc gtc aca aag agc ttc aac agg gga gag tgt      720
Gln Gly Leu Ser Ser Pro Val Thr Lys Ser Phe Asn Arg Gly Glu Cys
225                 230                 235                 240 tag                                                                  723
```

<210> SEQ ID NO 4
<211> LENGTH: 240
<212> TYPE: PRT
<213> ORGANISM: Homo sapiens

<400> SEQUENCE: 4

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Tyr Ser Ser Asn Asn Lys Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Thr Pro Pro Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 5
<211> LENGTH: 480
<212> TYPE: DNA
<213> ORGANISM: Homo sapiens
<220> FEATURE:
<221> NAME/KEY: CDS
<222> LOCATION: (1)..(480)
<223> OTHER INFORMATION:

<400> SEQUENCE: 5

```
atg aag aac cat ttg ctt ttc tgg gga gtc ctg gcg gtt ttt att aag        48
Met Lys Asn His Leu Leu Phe Trp Gly Val Leu Ala Val Phe Ile Lys
1               5                   10                  15 gct gtt cat gtg aaa gcc caa gaa gat gaa agg att gtt ctt gtt gac        96
Ala Val His Val Lys Ala Gln Glu Asp Glu Arg Ile Val Leu Val Asp
            20                  25                  30 aac aaa tgt aag tgt gcc cgg att act tcc agg atc atc cgt tct tcc       144
Asn Lys Cys Lys Cys Ala Arg Ile Thr Ser Arg Ile Ile Arg Ser Ser
        35                  40                  45 gaa gat cct aat gag gac att gtg gag aga aac atc cga att att gtt       192
Glu Asp Pro Asn Glu Asp Ile Val Glu Arg Asn Ile Arg Ile Ile Val
50                  55                  60 cct ctg aac aac agg gag aat atc tct gat ccc acc tca cca ttg aga       240
Pro Leu Asn Asn Arg Glu Asn Ile Ser Asp Pro Thr Ser Pro Leu Arg
65                  70                  75                  80 acc aga ttt gtg tac cat ttg tct gac ctc tgt aaa aaa tgt gat cct       288
Thr Arg Phe Val Tyr His Leu Ser Asp Leu Cys Lys Lys Cys Asp Pro
                85                  90                  95 aca gaa gtg gag ctg gat aat cag ata gtt act gct acc cag agc aat       336
Thr Glu Val Glu Leu Asp Asn Gln Ile Val Thr Ala Thr Gln Ser Asn
            100                 105                 110 atc tgt gat gaa gac agt gct aca gag acc tgc tac act tat gac aga       384
Ile Cys Asp Glu Asp Ser Ala Thr Glu Thr Cys Tyr Thr Tyr Asp Arg
        115                 120                 125 aac aag tgc tac aca gct gtg gtc cca ctc gta tat ggt ggt gag acc       432
Asn Lys Cys Tyr Thr Ala Val Val Pro Leu Val Tyr Gly Gly Glu Thr
130                 135                 140 aaa atg gtg gaa aca gcc tta acc cca gat gcc tgc tat cct gac taa       480
Lys Met Val Glu Thr Ala Leu Thr Pro Asp Ala Cys Tyr Pro Asp
145                 150                 155

<210> SEQ ID NO 6
<211> LENGTH: 159
<212> TYPE: PRT
<213> ORGANISM: Homo sapiens

<400> SEQUENCE: 6

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
130                 135                 140

Lys Met Val Glu Thr Ala Leu Thr Pro Asp Ala Cys Tyr Pro Asp
145                 150                 155
```

```
<210> SEQ ID NO 7
<211> LENGTH: 24
<212> TYPE: DNA
<213> ORGANISM: Artificial
<220> FEATURE:
<223> OTHER INFORMATION: an artificially synthesized sequence

<400> SEQUENCE: 7
ccaacggcaa caaagaaaag aacg                                              24

<210> SEQ ID NO 8
<211> LENGTH: 24
<212> TYPE: DNA
<213> ORGANISM: Artificial
<220> FEATURE:
<223> OTHER INFORMATION: an artificially synthesized sequence

<400> SEQUENCE: 8
aacatgctct ggccgagcca gtcg                                              24

<210> SEQ ID NO 9
<211> LENGTH: 24
<212> TYPE: DNA
<213> ORGANISM: Artificial
<220> FEATURE:
<223> OTHER INFORMATION: an artificially synthesized sequence

<400> SEQUENCE: 9
gcaagtccag ccagagtgtt ttat                                              24

<210> SEQ ID NO 10
<211> LENGTH: 24
<212> TYPE: DNA
<213> ORGANISM: Artificial
<220> FEATURE:
<223> OTHER INFORMATION: an artificially synthesized sequence

<400> SEQUENCE: 10
ctgtccttgc tgtcctgctc tgtg                                              24

<210> SEQ ID NO 11
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 11
aacagctcga gccaccatgg agtttgggct gag                                    33

<210> SEQ ID NO 12
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 12
agcggccagc cgccccgagc ctgtcgacag gc                                     32

<210> SEQ ID NO 13
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 13
```

```
atagaattcc accatggtgt tgcagaccca gg                                    32
```

```
<210> SEQ ID NO 14
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 14
ggagcaggcg gccgcacttc tccctctaac                                       30

<210> SEQ ID NO 15
<211> LENGTH: 24
<212> TYPE: DNA
<213> ORGANISM: Artificial
<220> FEATURE:
<223> OTHER INFORMATION: an artificially synthesized sequence

<400> SEQUENCE: 15
accattgaga accagatttg tgta                                             24

<210> SEQ ID NO 16
<211> LENGTH: 24
<212> TYPE: DNA
<213> ORGANISM: Artificial
<220> FEATURE:
<223> OTHER INFORMATION: an artificially synthesized sequence

<400> SEQUENCE: 16
tgtgtagcac ttgtttctgt cata                                             24

<210> SEQ ID NO 17
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 17
atgaattcca ccatgaagaa ccatttgc                                         28

<210> SEQ ID NO 18
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 18
tatctagatt agtcaggata gcaggc                                           26

<210> SEQ ID NO 19
<211> LENGTH: 1788
<212> TYPE: DNA
<213> ORGANISM: Homo sapiens
<220> FEATURE:
<221> NAME/KEY: CDS
<222> LOCATION: (1)..(1788)
<223> OTHER INFORMATION:

<400> SEQUENCE: 19 atg gag ttt ggg ctg agc tgg ctt ttt ctt gtg gct att tta aaa ggt        48
Met Glu Phe Gly Leu Ser Trp Leu Phe Leu Val Ala Ile Leu Lys Gly
1               5                   10                  15 gtc cag tgt gag gtg cag ctg ttg gag tct ggg gga ggc ttg gta cag        96
```

-continued

| | | |
|---|---|---|
| Val Gln Cys Glu Val Gln Leu Leu Glu Ser Gly Gly Gly Leu Val Gln<br>20  25  30 | | |
| ccg ggg ggg tcc ctg aga ctc tcc tgt gca gcc tct gga ttc acc ttt<br>Pro Gly Gly Ser Leu Arg Leu Ser Cys Ala Ala Ser Gly Phe Thr Phe<br>35  40  45 | 144 | |
| agc agc tat gcc atg agc tgg gtc cgc cag gct cca ggg aag ggg ctg<br>Ser Ser Tyr Ala Met Ser Trp Val Arg Gln Ala Pro Gly Lys Gly Leu<br>50  55  60 | 192 | |
| gag tgg gtc tca gct att agt ggt agt ggt tat acc aca tac tac gca<br>Glu Trp Val Ser Ala Ile Ser Gly Ser Gly Tyr Thr Thr Tyr Tyr Ala<br>65  70  75  80 | 240 | |
| gac tcc gtg aag ggc cgg ttc acc atc tcc aga gac aat tcc aag aac<br>Asp Ser Val Lys Gly Arg Phe Thr Ile Ser Arg Asp Asn Ser Lys Asn<br>85  90  95 | 288 | |
| acg ctg tat ctg caa atg aac agc ctg aga gcc gag gac acg gcc gta<br>Thr Leu Tyr Leu Gln Met Asn Ser Leu Arg Ala Glu Asp Thr Ala Val<br>100  105  110 | 336 | |
| tat tac tgt gcc aaa aaa ccg ggg gac tat ggt tcg ggg agt tat tac<br>Tyr Tyr Cys Ala Lys Lys Pro Gly Asp Tyr Gly Ser Gly Ser Tyr Tyr<br>115  120  125 | 384 | |
| ctt gac tac tgg ggc cag gga acc ctg gtc acc gtc tcc tca ggg agt<br>Leu Asp Tyr Trp Gly Gln Gly Thr Leu Val Thr Val Ser Ser Gly Ser<br>130  135  140 | 432 | |
| gca tcc gcc cca acc ctt ttc ccc ctc gtc tcc tgt gag aat tcc ccg<br>Ala Ser Ala Pro Thr Leu Phe Pro Leu Val Ser Cys Glu Asn Ser Pro<br>145  150  155  160 | 480 | |
| tcg gat acg agc agc gtg gcc gtt ggc tgc ctc gca cag gac ttc ctt<br>Ser Asp Thr Ser Ser Val Ala Val Gly Cys Leu Ala Gln Asp Phe Leu<br>165  170  175 | 528 | |
| ccc gac tcc atc act ttc tcc tgg aaa tac aag aac aac tct gac atc<br>Pro Asp Ser Ile Thr Phe Ser Trp Lys Tyr Lys Asn Asn Ser Asp Ile<br>180  185  190 | 576 | |
| agc agc acc cgg ggc ttc cca tca gtc ctg aga ggg ggc aag tac gca<br>Ser Ser Thr Arg Gly Phe Pro Ser Val Leu Arg Gly Gly Lys Tyr Ala<br>195  200  205 | 624 | |
| gcc acc tca cag gtg ctg ctg cct tcc aag gac gtc atg cag ggc aca<br>Ala Thr Ser Gln Val Leu Leu Pro Ser Lys Asp Val Met Gln Gly Thr<br>210  215  220 | 672 | |
| gac gaa cac gtg gtg tgc aaa gtc cag cac ccc aac ggc aac aaa gaa<br>Asp Glu His Val Val Cys Lys Val Gln His Pro Asn Gly Asn Lys Glu<br>225  230  235  240 | 720 | |
| aag aac gtg cct ctt cca gtg att gct gag ctg cct ccc aaa gtg agc<br>Lys Asn Val Pro Leu Pro Val Ile Ala Glu Leu Pro Pro Lys Val Ser<br>245  250  255 | 768 | |
| gtc ttc gtc cca ccc cgc gac ggc ttc ttc ggc aac ccc cgc aag tcc<br>Val Phe Val Pro Pro Arg Asp Gly Phe Phe Gly Asn Pro Arg Lys Ser<br>260  265  270 | 816 | |
| aag ctc atc tgc cag gcc acg ggt ttc agt ccc cgg cag att cag gtg<br>Lys Leu Ile Cys Gln Ala Thr Gly Phe Ser Pro Arg Gln Ile Gln Val<br>275  280  285 | 864 | |
| tcc tgg ctg cgc gag ggg aag cag gtg ggg tct ggc gtc acc acg gac<br>Ser Trp Leu Arg Glu Gly Lys Gln Val Gly Ser Gly Val Thr Thr Asp<br>290  295  300 | 912 | |
| cag gtg cag gct gag gcc aaa gag tct ggg ccc acg acc tac aag gtg<br>Gln Val Gln Ala Glu Ala Lys Glu Ser Gly Pro Thr Thr Tyr Lys Val<br>305  310  315  320 | 960 | |
| acc agc aca ctg acc atc aaa gag agc gac tgg ctc agc cag agc atg<br>Thr Ser Thr Leu Thr Ile Lys Glu Ser Asp Trp Leu Ser Gln Ser Met<br>325  330  335 | 1008 | |
| ttc acc tgc cgc gtg gat cac agg ggc ctg acc ttc cag cag aat gcg<br> | 1056 | |

|  |  |  |  |  |  |  |  |  |  |  |  |  |  |  |  |
|---|---|---|---|---|---|---|---|---|---|---|---|---|---|---|---|
| Phe | Thr | Cys | Arg | Val | Asp | His | Arg | Gly | Leu | Thr | Phe | Gln | Gln | Asn | Ala |
|  |  |  | 340 |  |  |  | 345 |  |  |  |  | 350 |  |  |  |

| tcc | tcc | atg | tgt | gtc | ccc | gat | caa | gac | aca | gcc | atc | cgg | gtc | ttc | gcc | 1104 |
|---|---|---|---|---|---|---|---|---|---|---|---|---|---|---|---|---|
| Ser | Ser | Met | Cys | Val | Pro | Asp | Gln | Asp | Thr | Ala | Ile | Arg | Val | Phe | Ala |  |
|  |  | 355 |  |  |  |  | 360 |  |  |  |  | 365 |  |  |  |  |

| atc | ccc | cca | tcc | ttt | gcc | agc | atc | ttc | ctc | acc | aag | tcc | acc | aag | ttg | 1152 |
|---|---|---|---|---|---|---|---|---|---|---|---|---|---|---|---|---|
| Ile | Pro | Pro | Ser | Phe | Ala | Ser | Ile | Phe | Leu | Thr | Lys | Ser | Thr | Lys | Leu |  |
|  | 370 |  |  |  | 375 |  |  |  |  | 380 |  |  |  |  |  |  |

| acc | tgc | ctg | gtc | aca | gac | ctg | acc | acc | tat | gac | agc | gtg | acc | atc | tcc | 1200 |
|---|---|---|---|---|---|---|---|---|---|---|---|---|---|---|---|---|
| Thr | Cys | Leu | Val | Thr | Asp | Leu | Thr | Thr | Tyr | Asp | Ser | Val | Thr | Ile | Ser |  |
| 385 |  |  |  |  | 390 |  |  |  |  | 395 |  |  |  |  | 400 |  |

| tgg | acc | cgc | cag | aat | ggc | gaa | gct | gtg | aaa | acc | cac | acc | aac | atc | tcc | 1248 |
|---|---|---|---|---|---|---|---|---|---|---|---|---|---|---|---|---|
| Trp | Thr | Arg | Gln | Asn | Gly | Glu | Ala | Val | Lys | Thr | His | Thr | Asn | Ile | Ser |  |
|  |  |  |  | 405 |  |  |  |  | 410 |  |  |  |  | 415 |  |  |

| gag | agc | cac | ccc | aat | gcc | act | ttc | agc | gcc | gtg | ggt | gag | gcc | agc | atc | 1296 |
|---|---|---|---|---|---|---|---|---|---|---|---|---|---|---|---|---|
| Glu | Ser | His | Pro | Asn | Ala | Thr | Phe | Ser | Ala | Val | Gly | Glu | Ala | Ser | Ile |  |
|  |  |  | 420 |  |  |  |  | 425 |  |  |  |  | 430 |  |  |  |

| tgc | gag | gat | gac | tgg | aat | tcc | ggg | gag | agg | ttc | acg | tgc | acc | gtg | acc | 1344 |
|---|---|---|---|---|---|---|---|---|---|---|---|---|---|---|---|---|
| Cys | Glu | Asp | Asp | Trp | Asn | Ser | Gly | Glu | Arg | Phe | Thr | Cys | Thr | Val | Thr |  |
|  |  | 435 |  |  |  |  | 440 |  |  |  |  | 445 |  |  |  |  |

| cac | aca | gac | ctg | ccc | tcg | cca | ctg | aag | cag | acc | atc | tcc | cgg | ccc | aag | 1392 |
|---|---|---|---|---|---|---|---|---|---|---|---|---|---|---|---|---|
| His | Thr | Asp | Leu | Pro | Ser | Pro | Leu | Lys | Gln | Thr | Ile | Ser | Arg | Pro | Lys |  |
| 450 |  |  |  |  | 455 |  |  |  |  | 460 |  |  |  |  |  |  |

| ggg | gtg | gcc | ctg | cac | agg | ccc | gat | gtc | tac | ttg | ctg | cca | cca | gcc | cgg | 1440 |
|---|---|---|---|---|---|---|---|---|---|---|---|---|---|---|---|---|
| Gly | Val | Ala | Leu | His | Arg | Pro | Asp | Val | Tyr | Leu | Leu | Pro | Pro | Ala | Arg |  |
| 465 |  |  |  |  | 470 |  |  |  |  | 475 |  |  |  |  | 480 |  |

| gag | cag | ctg | aac | ctg | cgg | gag | tcg | gcc | acc | atc | acg | tgc | ctg | gtg | acg | 1488 |
|---|---|---|---|---|---|---|---|---|---|---|---|---|---|---|---|---|
| Glu | Gln | Leu | Asn | Leu | Arg | Glu | Ser | Ala | Thr | Ile | Thr | Cys | Leu | Val | Thr |  |
|  |  |  |  | 485 |  |  |  |  | 490 |  |  |  |  | 495 |  |  |

| ggc | ttc | tct | ccc | gcg | gac | gtc | ttc | gtg | cag | tgg | atg | cag | agg | ggg | cag | 1536 |
|---|---|---|---|---|---|---|---|---|---|---|---|---|---|---|---|---|
| Gly | Phe | Ser | Pro | Ala | Asp | Val | Phe | Val | Gln | Trp | Met | Gln | Arg | Gly | Gln |  |
|  |  |  | 500 |  |  |  |  | 505 |  |  |  |  | 510 |  |  |  |

| ccc | ttg | tcc | ccg | gag | aag | tat | gtg | acc | agc | gcc | cca | atg | cct | gag | ccc | 1584 |
|---|---|---|---|---|---|---|---|---|---|---|---|---|---|---|---|---|
| Pro | Leu | Ser | Pro | Glu | Lys | Tyr | Val | Thr | Ser | Ala | Pro | Met | Pro | Glu | Pro |  |
|  |  | 515 |  |  |  |  | 520 |  |  |  |  | 525 |  |  |  |  |

| cag | gcc | cca | ggc | cgg | tac | ttc | gcc | cac | agc | atc | ctg | acc | gtg | tcc | gaa | 1632 |
|---|---|---|---|---|---|---|---|---|---|---|---|---|---|---|---|---|
| Gln | Ala | Pro | Gly | Arg | Tyr | Phe | Ala | His | Ser | Ile | Leu | Thr | Val | Ser | Glu |  |
|  | 530 |  |  |  |  | 535 |  |  |  |  | 540 |  |  |  |  |  |

| gag | gaa | tgg | aac | acg | ggg | gag | acc | tac | acc | tgc | gtg | gtg | gcc | cat | gag | 1680 |
|---|---|---|---|---|---|---|---|---|---|---|---|---|---|---|---|---|
| Glu | Glu | Trp | Asn | Thr | Gly | Glu | Thr | Tyr | Thr | Cys | Val | Val | Ala | His | Glu |  |
| 545 |  |  |  |  | 550 |  |  |  |  | 555 |  |  |  |  | 560 |  |

| gcc | ctg | ccc | aac | agg | gtc | acc | gag | agg | acc | gtg | gac | aag | tcc | acc | ggt | 1728 |
|---|---|---|---|---|---|---|---|---|---|---|---|---|---|---|---|---|
| Ala | Leu | Pro | Asn | Arg | Val | Thr | Glu | Arg | Thr | Val | Asp | Lys | Ser | Thr | Gly |  |
|  |  |  |  | 565 |  |  |  |  | 570 |  |  |  |  | 575 |  |  |

| aaa | ccc | acc | ctg | tac | aac | gtg | tcc | ctg | gtc | atg | tcc | gac | aca | gct | ggc | 1776 |
|---|---|---|---|---|---|---|---|---|---|---|---|---|---|---|---|---|
| Lys | Pro | Thr | Leu | Tyr | Asn | Val | Ser | Leu | Val | Met | Ser | Asp | Thr | Ala | Gly |  |
|  |  |  | 580 |  |  |  |  | 585 |  |  |  |  | 590 |  |  |  |

| acc | tgc | tac | tga |  |  |  |  |  |  |  |  |  |  |  |  | 1788 |
|---|---|---|---|---|---|---|---|---|---|---|---|---|---|---|---|---|
| Thr | Cys | Tyr |  |  |  |  |  |  |  |  |  |  |  |  |  |  |
|  |  | 595 |  |  |  |  |  |  |  |  |  |  |  |  |  |  |

<210> SEQ ID NO 20
<211> LENGTH: 595
<212> TYPE: PRT
<213> ORGANISM: Homo sapiens

<400> SEQUENCE: 20

| Met | Glu | Phe | Gly | Leu | Ser | Trp | Leu | Phe | Leu | Val | Ala | Ile | Leu | Lys | Gly |
|---|---|---|---|---|---|---|---|---|---|---|---|---|---|---|---|
| 1 |  |  |  | 5 |  |  |  |  | 10 |  |  |  |  | 15 |  |

| Val | Gln | Cys | Glu | Val | Gln | Leu | Leu | Glu | Ser | Gly | Gly | Gly | Leu | Val | Gln |
|---|---|---|---|---|---|---|---|---|---|---|---|---|---|---|---|
|  |  |  | 20 |  |  |  |  | 25 |  |  |  |  | 30 |  |  |

-continued

```
Pro Gly Gly Ser Leu Arg Leu Ser Cys Ala Ala Ser Gly Phe Thr Phe
            35                  40                  45

Ser Ser Tyr Ala Met Ser Trp Val Arg Gln Ala Pro Gly Lys Gly Leu
 50                  55                  60

Glu Trp Val Ser Ala Ile Ser Gly Ser Gly Tyr Thr Thr Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Lys Lys Pro Gly Asp Tyr Gly Ser Gly Ser Tyr Tyr
            115                 120                 125

Leu Asp Tyr Trp Gly Gln Gly Thr Leu Val Thr Val Ser Ser Gly Ser
            130                 135                 140

Ala Ser Ala Pro Thr Leu Phe Pro Leu Val Ser Cys Glu Asn Ser Pro
145                 150                 155                 160

Ser Asp Thr Ser Ser Val Ala Val Gly Cys Leu Ala Gln Asp Phe Leu
                165                 170                 175

Pro Asp Ser Ile Thr Phe Ser Trp Lys Tyr Lys Asn Asn Ser Asp Ile
            180                 185                 190

Ser Ser Thr Arg Gly Phe Pro Ser Val Leu Arg Gly Gly Lys Tyr Ala
            195                 200                 205

Ala Thr Ser Gln Val Leu Leu Pro Ser Lys Asp Val Met Gln Gly Thr
            210                 215                 220

Asp Glu His Val Val Cys Lys Val Gln His Pro Asn Gly Asn Lys Glu
225                 230                 235                 240

Lys Asn Val Pro Leu Pro Val Ile Ala Glu Leu Pro Pro Lys Val Ser
                245                 250                 255

Val Phe Val Pro Pro Arg Asp Gly Phe Phe Gly Asn Pro Arg Lys Ser
            260                 265                 270

Lys Leu Ile Cys Gln Ala Thr Gly Phe Ser Pro Arg Gln Ile Gln Val
            275                 280                 285

Ser Trp Leu Arg Glu Gly Lys Gln Val Gly Ser Gly Val Thr Thr Asp
            290                 295                 300

Gln Val Gln Ala Glu Ala Lys Glu Ser Gly Pro Thr Thr Tyr Lys Val
305                 310                 315                 320

Thr Ser Thr Leu Thr Ile Lys Glu Ser Asp Trp Leu Ser Gln Ser Met
            325                 330                 335

Phe Thr Cys Arg Val Asp His Arg Gly Leu Thr Phe Gln Gln Asn Ala
            340                 345                 350

Ser Ser Met Cys Val Pro Asp Gln Asp Thr Ala Ile Arg Val Phe Ala
            355                 360                 365

Ile Pro Pro Ser Phe Ala Ser Ile Phe Leu Thr Lys Ser Thr Lys Leu
            370                 375                 380

Thr Cys Leu Val Thr Asp Leu Thr Thr Tyr Asp Ser Val Thr Ile Ser
385                 390                 395                 400

Trp Thr Arg Gln Asn Gly Glu Ala Val Lys Thr His Thr Asn Ile Ser
                405                 410                 415

Glu Ser His Pro Asn Ala Thr Phe Ser Ala Val Gly Glu Ala Ser Ile
            420                 425                 430

Cys Glu Asp Asp Trp Asn Ser Gly Glu Arg Phe Thr Cys Thr Val Thr
            435                 440                 445

His Thr Asp Leu Pro Ser Pro Leu Lys Gln Thr Ile Ser Arg Pro Lys
```

```
                    450                 455                 460
Gly Val Ala Leu His Arg Pro Asp Val Tyr Leu Leu Pro Pro Ala Arg
465                 470                 475                 480

Glu Gln Leu Asn Leu Arg Glu Ser Ala Thr Ile Thr Cys Leu Val Thr
                485                 490                 495

Gly Phe Ser Pro Ala Asp Val Phe Val Gln Trp Met Gln Arg Gly Gln
            500                 505                 510

Pro Leu Ser Pro Glu Lys Tyr Val Thr Ser Ala Pro Met Pro Glu Pro
        515                 520                 525

Gln Ala Pro Gly Arg Tyr Phe Ala His Ser Ile Leu Thr Val Ser Glu
    530                 535                 540

Glu Glu Trp Asn Thr Gly Glu Thr Tyr Thr Cys Val Val Ala His Glu
545                 550                 555                 560

Ala Leu Pro Asn Arg Val Thr Glu Arg Thr Val Asp Lys Ser Thr Gly
                565                 570                 575

Lys Pro Thr Leu Tyr Asn Val Ser Leu Val Met Ser Asp Thr Ala Gly
            580                 585                 590

Thr Cys Tyr
        595

<210> SEQ ID NO 21
<211> LENGTH: 726
<212> TYPE: DNA
<213> ORGANISM: Homo sapiens
<220> FEATURE:
<221> NAME/KEY: CDS
<222> LOCATION: (1)..(726)
<223> OTHER INFORMATION:

<400> SEQUENCE: 21 atg gtg ttg cag acc cag gtc ttc att tct ctg ttg ctc tgg atc tct        48
Met Val Leu Gln Thr Gln Val Phe Ile Ser Leu Leu Leu Trp Ile Ser
1               5                   10                  15 ggt gcc tac ggg gac atc gtg atg acc cag tct cca gac tcc ctg gct        96
Gly Ala Tyr Gly Asp Ile Val Met Thr Gln Ser Pro Asp Ser Leu Ala
            20                  25                  30 gtg tct ctg ggc gag agg gcc acc atc aac tgc aag tcc agc cag agt       144
Val Ser Leu Gly Glu Arg Ala Thr Ile Asn Cys Lys Ser Ser Gln Ser
        35                  40                  45 gtt tta tac agc tcc aac aat aag aac tac tta gct tgg tac cag cag       192
Val Leu Tyr Ser Ser Asn Asn Lys Asn Tyr Leu Ala Trp Tyr Gln Gln
    50                  55                  60 aaa cca gga cag cct cct aag ttg ctc att tac tgg gca tct acc cgg       240
Lys Pro Gly Gln Pro Pro Lys Leu Leu Ile Tyr Trp Ala Ser Thr Arg
65                  70                  75                  80 gaa tcc ggg gtc cct gac cga ttc agt ggc agc ggg tct ggg aca gat       288
Glu Ser Gly Val Pro Asp Arg Phe Ser Gly Ser Gly Ser Gly Thr Asp
                85                  90                  95 ttc act ctc acc atc agc agc ctg cag gct gaa gat gtg gca gtt tat       336
Phe Thr Leu Thr Ile Ser Ser Leu Gln Ala Glu Asp Val Ala Val Tyr
            100                 105                 110 tac tgt cag caa tat tat act act ctt ccg ctc act ttc ggc gga ggg       384
Tyr Cys Gln Gln Tyr Tyr Thr Thr Leu Pro Leu Thr Phe Gly Gly Gly
        115                 120                 125 acc aag gtg gag atc aaa cga act gtg gct gca cca tct gtc ttc atc       432
Thr Lys Val Glu Ile Lys Arg Thr Val Ala Ala Pro Ser Val Phe Ile
    130                 135                 140 ttc ccg cca tct gat gag cag ttg aaa tct gga act gcc tct gtt gtg       480
Phe Pro Pro Ser Asp Glu Gln Leu Lys Ser Gly Thr Ala Ser Val Val
145                 150                 155                 160
```

```
tgc ctg ctg aat aac ttc tat ccc aga gag gcc aaa gta cag tgg aag    528
Cys Leu Leu Asn Asn Phe Tyr Pro Arg Glu Ala Lys Val Gln Trp Lys
                165                 170                 175 gtg gat aac gcc ctc caa tcg ggt aac tcc cag gag agt gtc aca gag    576
Val Asp Asn Ala Leu Gln Ser Gly Asn Ser Gln Glu Ser Val Thr Glu
            180                 185                 190 cag gac agc aag gac agc acc tac agc ctc agc agc acc ctg acg ctg    624
Gln Asp Ser Lys Asp Ser Thr Tyr Ser Leu Ser Ser Thr Leu Thr Leu
        195                 200                 205 agc aaa gca gac tac gag aaa cac aaa gtc tac gcc tgc gaa gtc acc    672
Ser Lys Ala Asp Tyr Glu Lys His Lys Val Tyr Ala Cys Glu Val Thr
    210                 215                 220 cat cag ggc ctg agc tcg ccc gtc aca aag agc ttc aac agg gga gag    720
His Gln Gly Leu Ser Ser Pro Val Thr Lys Ser Phe Asn Arg Gly Glu
225                 230                 235                 240 tgt tag                                                            726
Cys
```

<210> SEQ ID NO 22
<211> LENGTH: 241
<212> TYPE: PRT
<213> ORGANISM: Homo sapiens

<400> SEQUENCE: 22

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Tyr Ser Ser Asn Asn Lys Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Thr Thr Leu Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

```
<210> SEQ ID NO 23
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 23
caacaggcag gcaggggcag caag                                           24

<210> SEQ ID NO 24
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 24
agcataatta aagccaagga ggag                                           24

<210> SEQ ID NO 25
<211> LENGTH: 68
<212> TYPE: DNA
<213> ORGANISM: Artificial
<220> FEATURE:
<223> OTHER INFORMATION: an artificially synthesized sequence

<400> SEQUENCE: 25
cctgatcatg aagacgtcga ctagtccgga tccccgggag ctcgagcgct ctagatcttt    60
aattaagg                                                             68

<210> SEQ ID NO 26
<211> LENGTH: 76
<212> TYPE: DNA
<213> ORGANISM: Artificial
<220> FEATURE:
<223> OTHER INFORMATION: an artificially synthesized sequence

<400> SEQUENCE: 26
cgcgccttaa ttaaagatct agagcgctcg agctcccggg gatccggact agtcgacgtc    60
ttcatgatca ggccgg                                                    76

<210> SEQ ID NO 27
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 27
gaggaattcc accatgaaga acc                                            23

<210> SEQ ID NO 28
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 28
gaggcggccg cttagtcagg atagcag                                        27

<210> SEQ ID NO 29
<211> LENGTH: 32
<212> TYPE: DNA
<213> ORGANISM: Artificial
```

```
<220> FEATURE:
<223> OTHER INFORMATION: an artificially synthesized primer sequence

<400> SEQUENCE: 29
aaaagcggcc gcgatcataa tcagccatac ca                              32

<210> SEQ ID NO 30
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 30
aaaactcgag aagcttagac atgataagat acattg                          36

<210> SEQ ID NO 31
<211> LENGTH: 12
<212> TYPE: DNA
<213> ORGANISM: Artificial
<220> FEATURE:
<223> OTHER INFORMATION: an artificially synthesized linker sequence

<400> SEQUENCE: 31
cccggatccg gg                                                    12
```